US008399235B2

(12) United States Patent
Frank et al.

(10) Patent No.: US 8,399,235 B2
(45) Date of Patent: Mar. 19, 2013

(54) METHODS AND MATERIALS FOR REDUCING BIOFILMS

(75) Inventors: Kristi L. Frank, Minneapolis, MN (US); Robin Patel, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 366 days.

(21) Appl. No.: 12/664,574

(22) PCT Filed: Jun. 13, 2008

(86) PCT No.: PCT/US2008/066913
§ 371 (c)(1),
(2), (4) Date: Jun. 11, 2010

(87) PCT Pub. No.: WO2008/157350
PCT Pub. Date: Dec. 24, 2008

(65) Prior Publication Data
US 2010/0254967 A1    Oct. 7, 2010

Related U.S. Application Data

(60) Provisional application No. 60/944,019, filed on Jun. 14, 2007.

(51) Int. Cl.
*C12N 9/24* (2006.01)
(52) U.S. Cl. ...................................... 435/200; 536/23.2
(58) Field of Classification Search ............... 424/94.61; 435/200; 536/23.2
See application file for complete search history.

(56) References Cited

U.S. PATENT DOCUMENTS

| 4,683,195 A | 7/1987 | Mullis et al. |
| 2006/0246049 A1 | 11/2006 | Kaplan |
| 2007/0009505 A1 | 1/2007 | Arscott et al. |

OTHER PUBLICATIONS

Accession No. AZ671097 (Dec. 14, 2000).*
Cramton et al., "The intercellular adhesion (ica) locus is present in *Staphylococcus aureus* and is required for biofilm formation," *Infect. Immun.*, 1999, 67:5427-5433.
Deighton et al., "Methods for studying biofilms produced by *Staphylococcus epidermidis*," *Methods Enzymol.*, 2001, 336:177-195.
Dobinsky et al., "Glucose-related dissociation between icaADBC transcription and biofilm expression by *Staphylococcus epidermidis*: evidence for an additional factor required for polysaccharide intercellular adhesin synthesis," *J. Bacteriol.*, 2003, 185:2879-2886.
Frank and Patel, "Activity of sodium metabisulfite against planktonic and biofilm *Staphylococcus* species," *Diagn. Microbiol. Infect. Dis.*, 2007, 57:355-359.
Frank et al., "icaA Is Not a Useful Diagnostic Marker for Prosthetic Joint Infection," *J. Clin. Microbiol.*, 2004, 42:4846-4849.
Frank et al., "In Vitro Effects of Antimicrobial Agents on Planktonic and Biofilm Forms of *Staphylococcus lugdunensis* Clinical Isolates," *Antimicrob. Agents Chemother.*, 2007, 51:888-895.
Gotz et al., "Protoplast transformation of *Staphylococcus carnosus* by plasmid DNA ," *Mol. Gen. Genet.*, 1983, 189:340-342.
Heilmann et al., "Molecular basis of intercellular adhesion in the biofilm-forming *Staphylococcus epidermidis*," *Mol. Microbiol.*, 1996, 20:1083-1091.
Henrissat, "A classification of glycosyl hydrolases based on amino acid sequence similarities," *Biochem. J.*, 1991, 280(Pt 2):309-316.
Itoh et al., "Depolymerization of {beta} -1,6-N-Acetyl-D-Glucosamine Disrupts the Integrity of Diverse Bacterial Biofilms," *J. Bacteriol.*, 2005, 187:382-387.
Jefferson and Cerca, "Bacterial-bacterial cell interactions in biofilms: detection of polysaccharide intercellular adhesins by blotting and confocal microscopy," *Methods Mol. Biol.*, 2006 341:119-126.
Kaplan et al., "Detachment of *Actinobacillus actinomycetemcomitans* biofilm cells by an endogenous beta-hexosaminidase activity," *J. Bacteriol.*, 2003, 185:4693-4698.
Kaplan et al., "Enzymatic Detachment of *Staphylococcus epidermidis* Biofilms," *Antimicrob. Agents Chemother.*, 2004, 48:2633-2636.
Kaplan et al., "Genes Involved in the Synthesis and Degradation of Matrix Polysaccharide in *Actinobacillus actinomycetemcomitans* and *Actinobacillus pleuropneumoniae* Biofilms," *J. Bacteriol.*, 2004, 186:8213-8220.
Knobloch et al., "Alcoholic ingredients in skin disinfectants increase biofilm expression of *Staphylococcus epidermidis*," *J. Antimicrob. Chemother.*, 2002, 49:683-687.
Knobloch et al., "Biofilm Formation by *Staphylococcus epidermidis* Depends on Functional RsbU, an Activator of the sigB Operon: Differential Activation Mechanisms Due to Ethanol and Salt Stress," *J. Bacteriol.*, 2001, 183:2624-2633.
Knobloch et al., "Evaluation of different detection methods of biofilm formation in *Staphylococcus aureus*," *Med. Microbiol. Immunol.*, 2002, 191:101-106.
Kreiswirth et al., "The toxic shock syndrome exotoxin structural gene is not detectably transmitted by a prophage," *Nature*, 1983, 305:709-712.
Lim et al., "Control of Glucose- and NaCl-Induced Biofilm Formation by rbf in *Staphylococcus aureus*," *J. Bacteriol.*, 2004, 186:722-729.
Mack et al., "The intercellular adhesin involved in biofilm accumulation of *Staphylococcus epidermidis* is a linear beta-1,6-linked glucosaminoglycan: purification and structural analysis," *J. Bacteriol.*, 1996, 178:175-183.
Maira-Litran et al., "Comparative Opsonic and Protective Activities of *Staphylococcus aureus* Conjugate Vaccines Containing Native or Deacetylated Staphylococcal Poly-N-Acetyl-{beta} -(1-6)-Glucosamine," *Infect. Immun.*, 2005, 73:6752-6762.
Moretro et al., "Biofilm Formation and the Presence of the Intercellular Adhesion Locus ica among Staphylococci from Food and Food Processing Environments," *Appl. Environ. Microbiol.*, 2003, 69:5648-5655.
Parise et al, "Role of a Putative Polysaccharide Locus in *Bordetella* Biofilm Development," *J. Bacteriol.*, 2007, 189:750-760.

(Continued)

*Primary Examiner* — Tekchand Saidha
(74) *Attorney, Agent, or Firm* — Fish & Richardson P.C.

(57) ABSTRACT

This document provides methods and materials related to reducing biofilms. For example, enzymes (e.g., glycosyl hydrolases), nucleic acid molecules encoding enzymes, host cells containing nucleic acid encoding enzymes, and methods for using enzymes to reduce biofilms and infections associated with biofilms are provided.

4 Claims, 14 Drawing Sheets

OTHER PUBLICATIONS

Potvin et al., "In vivo functional genomics of *Pseudomonas aeruginosa* for high-throughput screening of new virulence factors and antibacterial targets," *Environ Microbiol.*, 2003, 5(12):1294-1308.

Ramasubbu et al.," Structural analysis of dispersin B, a biofilm-releasing glycoside hydrolase from the periodontopathogen *Actinobacillus actinomycetemcomitans*," *J Mol Biol.*, 2005, 349(3):475-486.

Sambrook et al., Molecular Cloning, second edition, 1989, Cold Spring harbor Laboratory, Plainview, NY, sections 7.39-7.52.

Sandoe et al., "Ventriculoperitoneal shunt infection caused by *Staphylococcus lugdunensis*," *Clin. Microbiol. Infect.*, 2001, 7:385-387.

Sarkar et al., "Restriction-site PCR: a direct method of unknown sequence retrieval adjacent to a known locus by using universal primers," *PCR Methods Appl.*, 1993, 2:318-322.

Sharp and Pogliano, "From the Cover: An in vivo membrane fusion assay implicates SpoIIIE in the final stages of engulfment during *Bacillus subtilis* sporulation," *Proc. Natl. Acad. Sci. U.S.A.*, 1999, 96:14553-14558.

Tews et al., "Bacterial chitobiase Structure Provides Insight into Catalytic Mechanism and the Basis of Tay-Sachs Disease," *Nat. Struct. Biol.*, 1996, 3:638-648.

Wang et al., "The pgaABCD Locus of *Escherichia coli* Promotes the Synthesis of a Polysaccharide Adhesin Required for Biofilm Formation," *J. Bacteriol.*, 2004, 186:2724-2734.

International Search Report and Written Opinion of the International Searching Authority from PCT/US2008/066913, mailed Dec. 29, 2008, 9 pages.

International Preliminary Report on Patentability, from PCT/US2008/066913, issued Dec. 17, 2009, 6 pages.

GenBank Accession No. AF246927, dated Mar. 13, 2001, 1 page.
GenBank Accession No. AF246926, dated Mar. 13, 2001, 2 pages.
GenBank Accession No. NC_007795, dated Nov. 1, 2010, 64 pages.
Accession No. COG3525.2, 1 page ; reported created date Oct. 7, 2002.
Accession No. pfam00728, 1 page; reported created date Dec. 21, 2011 (older versions existed prior to Jun. 14, 2007).
GenBank Accession No. EF546620, dated Sep. 24, 2007, 3 pages.
GenBank Accession No. EF546621, dated Sep. 24, 2007, 3 pages.
GenBank Accession No. EF546622, dated Sep. 24, 2007, 3 pages.
GenBank Accession No. EF546623, dated Sep. 24, 2007, 3 pages.
GenBank Accession No. EF546624, dated Sep. 24, 2007, 3 pages.

Bateman et al., "The G5 domain: a potential N-acetylglucosamine recognition domain involved in biofilm formation," *Bioinformatics*, 2005, 21(8):1301-1303.

Bendtsen et al., "Improved prediction of signal peptides: SignalP 3.0.," *J. Mol. Biol.*, 2004, 340:783-795.

Chaignon et al., "Susceptibility of staphylococcal biofilms to enzymatic treatments depends on their chemical composition," *Appl. Microbiol. Biotechnol.*, 2007, 75(1):125-132.

Christensen et al., "Adherence of coagulase-negative staphylococci to plastic tissue culture plates: a quantitative model for the adherence of staphylococci to medical devices," *J. Clin. Microbiol.*, 1985, 22:996-1006.

Christensen et al., "Adherence of slime-producing strains of Staphylococcus epidermidis to smooth surfaces," *Infect. Immun.*, 1982, 37:318-326.

Conlon et al., "icaR Encodes a Transcriptional Repressor Involved in Environmental Regulation of ica Operon Expression and Biofilm Formation in Staphylococcus epidermidis," *J. Bacteriol.*, 2002, 184:4400-4408.

* cited by examiner

Figure 4

ATGAAAAAGCTTAGTGCCATTATTGTTATTTTATTACTTATTGTATTCACTT
TCTTTCCTAAGCATAGTAAGCAATCTGATATTGAAAAGGGTATTTCTATTG
ATATTGCACGGACGCATTATACTAAAGAGAGTATTAAGAAAATCATCGGC
GAGCTTAGCCGTGTCAATGGGCGTTATCTACAATTACACCTTGCTGACAAT
GACAATTATAGTATTTACTCAAATGTCTTAGGTCAAACGTCTACCCATTCA
AATCACTATTACCTCACAAAAGCAGAATTGCGTGAGCTTGTTCAATATGC
CAATAAACACCATGTCCAGCTTATTCCTGAATTAGACTTCCCTGCACATTC
AAAAGCCATGCTGACGTTACTCCATAAACATCATCCCTCTCAATATCGAC
AGGTTGTTTCTAGCTATGATAATACAATGCTTGATTTTCAACAAAATCAGA
CAGCGCTTGATGTATCTCGTCAGTTAATCAATGAAGTTGCTGATATTTTCT
ATCAAACACCGTATAAAGACAATTTAAAAATGGTTATCGGTGGAGATGAG
GTACCTGGTGGAGGCGCACAGCAACGTGATTTTGTTTCATACATGAATCA
GCTTGCAGACACTGTCCAAGCAAAGCATTATACGCCTAAGATGTGGAATG
ATTCTTTGACACATGAAGGACTCAAAAATTTAAATCACAGCATTATTATA
TGTATTGGCATCAACCATCCAAACAGTCACCATCGCCAACTGACTTTTTCA
CTAACCACTTTATGGTCGAAAATTTTAATCGTTCTGTTTACTACGTCTTTCC
TAGAGCACAGCAAAGCACACATTCGTTAGCTAAGCAGAAAGCTGATATTG
CCGACACACGTTTAACAGATTTAATACAGCTAATATGCGTAAAGACCCG
CATTTCAATAGTTATATTAATGGTGAATATCTCACATTTTGGGGAGAATTT
GCTTCAGATTTAAAACAGACCAATTTAATCGAGTATGTATATAAGTTTATT
CGCATTTATTTTAATTCCTAA

FIGURE 7

MKKLSAIIVILLLIVFTFFPKHSKQSDIEKGISIDIARTHYTKESIKKIIGELSRVN
GRYLQLHLADNDNYSIYSNVLGQTSTHSNHYYLTKAELRELVQYANKHHVQ
LIPELDFPAHSKAMLTLLHKHHPSQYRQVVSSYDNTMLDFQQNQTALDVSR
QLINEVADIFYQTPYKDNLKMVIGGDEVPGGGAQQRDFVSYMNQLADTVQA
KHYTPKMWNDSLTHEGLKNLNHSIIIMYWHQPSKQSPSPTDFFTNHFMVENF
NRSVYYVFPRAQQSTHSLAKQKADIADTRLTDFNTANMRKDPHFNSYINGEY
LTFWGEFASDLKQTNLIEYVYKFIRIYFNS

FIGURE 8

```
A:  A. pleuropneumonaie|46143406|re (SEQ ID NO:3)
B:  A. actinomycetemcomitans|304209 (SEQ ID NO:4)
C:  S. lugdunensis polypeptide (SEQ ID NO:2)

A:  MKKAITLFTLLCAVLLSFSTATYANAMDLPKKESGLTLDIARRFYTVDTI  50
B:  ----------NCCVK---GNSIYP--QKTSTKQTGLMLDIARHFYSPEVI  35
C:  ----MKKLSAIIVILLLIVFTFFPKHSKQSDIEKGISIDIARTHYTKESI  46
           :         : .    . .   :.*: :****  .*:  : *

A:  KQFIDTIHQAGGTFLHLHFSDHENYALESSYLEQREENATE-KNGTYFNP  99
B:  KSFIDTISLSGGNFLHLHFSDHENYAIESHLLNQRAENAVQGKDGIYINP  85
C:  KKIIGELSRVNGRYLQLHLADNDNYSIYSNVLGQTS-------------T  83
    *.:*.  :    .* :*:**::*::**::  *    *          .

A:  KTNKPFLTYKQLNEIIYYAKERNIEIVPEVDSPNHMTAIFDLLTLKHGKE  149
B:  YTGKPFLSYRQLDDIKAYAKAKGIELIPELDSPNHMTAIFKLVQKDRGVK  135
C:  HSNHYYLTKAELRELVQYANKHHVQLIPELDFPAHSKAMLTLLHKHHPSQ  133
    :.: :*:   :*  :: **:  :   :::**:*  * * .*:: *:  .:  :

A:  YVKGLKSPYIAEEIDINNPEAVEVIKTLIGEVIYIFGHS----SRHFHIG  195
B:  YLQGLKSRQVDDEIDITNADSITFMQSLMSEVIDIFGDT----SQHFHIG  181
C:  YRQVVSSYDNTMLDFQQNQTALDVSRQLINEVADIFYQTPYKDNLKMVIG  183
    * :  :.*       *    ::  .  : *:.**  ** .:     . :: **

A:  GDEFSYAVENNHEFIRYVNTLNDFINSKGLITRVWNDGLIKNNLSELNKN  245
B:  GDEFGYSVESNHEFITYANKLSYFLEKKGLKTRMWNDGLIKNTFEQINPN  231
C:  GDEVPGGGAQQRDFVSYMNQLADTVQAKHYTPKMWNDSLTHEGLKNLNHS  233
    ***.  .   .::*: * * *   ::  *   .::***.* ::  :.::* .

A:  IEITYWSYDGDAQAKEDIQYRREIRADLPELLANGFKVLNYNSYYLYFVP  295
B:  IEITYWSYDGTQDKNEAAERRDMRVSLPELLAKGFTVLNYNSYYLYIVP  281
C:  IIIMYWHQPSKQSP------------SPTDFFTNHFMVENFNRSVYYVFP  271
    *  * **     . .                . .::::: * * *:*    *..*

A:  KSGSNIHNDGKYAAEDVLNNWTLGKWDGKNSSNHVQNTQNIIGSSLSIWG  345
B:  KASPTFSQDAAFAAKDVIKNWDLGVWDGRNTKNRVQNTHEIAGAALSIWG  331
C:  RAQQSTHSLAKQKAD--IADTRLTDFNTANMRKDPHFNSYINGEYLTFWG  319
    ::  .  ..    *.  :  :   *   ::   * :   :  .  * *  *::**

A:  ERSSALNEQTIQQASKNLLKAVIQKTNDPKSH  377
B:  EDAKALKDETIQKNTKSLLEAVIHKTNGDE--  361
C:  EFASDLKQTNLIEYVYKFIRIYFNS-------  344
    *  :. *::  .: :    .::.   ::.
```

FIGURE 9

```
ATGAAAAAGCTTAGTGCCATTATTGTTATTTTATTACTTATTGTATTCACTTTCTTTCCTAAGCA
TAGTAAGCAAGCTGATATTGAAAAGGGTATTTCTATTGATATTGCACGGACGCATTATACTAA
AGATAGCATTAAGAAAATCATCGGCGAGCTTAGCCGTGTCAATGGGCGTTATCTACAATTAC
ACCTTGCTGACAATGACAATTATAGTATTTACTCAAATGTCTTAGGTCAAACGTCTACCCATT
CAAATCACTATTACCTCACAAAAGCAGAATTGCGTGAGCTTGTTCAATATGCCAATAAACACC
ATGTCCAGCTTATTCCTGAATTAGACTTCCCTGCACATTCAAAAGCCATGCTGACGTTACTCC
ATAAACATCATCCCTCTCAATATCGACAGGTTGTTTCTAGCTATGATAATACAATGCTTGATTT
TCAACAAAATCAGACAGCGCTTGATGTATCTCGTCAGTTAATCAATGAAGTTGCTGATATTTT
CTATCAAACACCGTATAAAGACAATTTAAAAATGGTTATCGGTGGAGATGAGGTACCTGGTG
GAGGCGCACAGCAACGTGATTTTGTTTCATACATGAATCAGCTTGCAGACACTGTCCAAGCA
AAGCATTATACGCCTAAGATGTGGAATGACTCTTTGACACATGAAGGACTCAAAAATTTAAAT
CACAGCATTATTATTATGTATTGGCATCAACCATCCAAACAGTCACCATCGCCAACTGACTTT
TTCACTAACCACTTTATGGTCGAAAATTTTAATCGTTCTGTTTACTATGTCTTTCCTAGAGCAC
AGCAAAGCACACATTCGTTAGCTAAGCAGAAAGCTGATATTGCCGACACACGTTTAACAGAT
TTTAATACAGCTAATATGCGTAAAGATCCGCATTTCAATAGTTATATTAATGGTGAATATCTCA
CATTTTGGGGAGAATTTGCTTCAGATTTAAAACAGACCAATTTAATCGAGTATGTATATAAGTT
TATTCGCATTTATTTTAATTCCTAA
```

FIGURE 10

MKKLSAIIVILLLIVFTFFFPKHSKQADIEKGISIDIARTHYTKDSIKKIIGELSRVNGRYLQLHLADNDN
YSIYSNVLGQTSTHSNHYYLTKAELRELVQYANKHHVQLIPELDFPAHSKAMLTLLHKHHPSQYR
QVVSSYDNTMLDFQQNQTALDVSRQLINEVADIFYQTPYKDNLKMVIGGDEVPGGGAQQRDFV
SYMNQLADTVQAKHYTPKMWNDSLTHEGLKNLNHSIIMYWHQPSKQSPSPTDFFTNHFMVENF
NRSVYYVFPRAQQSTHSLAKQKADIADTRLTDFNTANMRKDPHFNSYINGEYLTFWGEFASDLK
QTNLIEYVYKFIRIYFNS

FIGURE 11

METHODS AND MATERIALS FOR REDUCING BIOFILMS

CROSS-REFERENCE TO RELATED APPLICATIONS

This application is a National Stage application under 35 U.S.C. 371 and claims benefit under 35 U.S.C. 119(a) of International Application No. PCT/US2008/066913, having an International Filing Date of Jun. 13, 2008, which claims the benefit of U.S. Provisional Application Ser. No. 60/944, 019, filed Jun. 14, 2007. The disclosures of the prior applications are incorporated by reference in their entirety.

BACKGROUND

1. Technical Field

This document relates to methods and materials involved in reducing biofilms. For example, this document provides enzymes (e.g., glycosyl hydrolases) and methods for using enzymes to reduce biofilms.

2. Background Information

Bacteria growing in biofilms are estimated to be involved in greater than 60 percent of all human bacterial infections. Biofilms are dynamic populations of bacteria in a surface-associated mode of growth that are covered in a protective, self-excreted extracellular polymeric substance (EPS) matrix. Biofilms provide protection against harsh environmental conditions, traditional antimicrobial therapies, and host immune defenses, thus making biofilm-associated infections difficult to treat. Biofilm-associated infections of indwelling medical devices (e.g., intravascular and urinary catheters, prosthetic heart valves, prosthetic joint implants, and hardware) represent a particularly important health problem, as removal and replacement of infected devices is often required.

The EPS matrix of a diverse number of biofilm-forming bacterial species can be composed of chains of polymeric β-1,6-linked N-acetyl-glucosamine (PNAG). Biofilm-forming strains of *Staphylococcus aureus, S. epidermidis, Bordetella* spp., *Actinobacillus* spp., and *Escherichia coli* are known to utilize PNAG as a major component of their EPS biofilm matrix (Cramton et al., *Infect. Immun.*, 67:5427-5433 (1999); Kaplan et al., *J. Bacteriol.*, 186:8213-8220 (2004); Mack et al., *J. Bacteriol.*, 178:175-183 (1996); Parise et al., *J. Bacteriol.*, 189:750-760 (2007); and Wang et al., *J. Bacteriol.*, 186:2724-2734 (2004)). The N-acetyl-β-hexosaminidase, dispersin B, first purified from the Gram negative periodontal pathogen *Actinobacillus actinomycetemcomitans* (Kaplan et al., *J. Bacteriol.*, 185:4693-8 (2003)), can cleave the β-1,6-linkages of PNAG in the biofilm matrices of *Staphylococcus* spp., *Yersinia pestis, Actinobacillus* spp., *Bordetella* spp., and *E. coli* (Itoh et al., *J. Bacteriol.*, 187:382-387 (2005); Kaplan et al., *J. Bacteriol.*, 185:4693-8 (2003); Kaplan et al., *Antimicrob. Agents Chemother.*, 48:2633-2636 (2004); Kaplan et al., *J. Bacteriol.*, 186:8213-8220 (2004); and Parise et al, *J. Bacteriol.*, 189:750-760 (2007)).

SUMMARY

This document provides methods and materials related to reducing biofilms. For example, this document provides enzymes (e.g., glycosyl hydrolases), nucleic acid molecules encoding enzymes, host cells containing nucleic acid encoding enzymes, and methods for using enzymes to reduce biofilms and infections associated with biofilms. Reducing biofilms and infections associated with biofilms can allow clinicians to treat patients effectively and can help reduce the incidence of infections in mammals (e.g., mammals containing or using a medical device that is susceptible to biofilms).

*S. lugdunensis* is an atypically virulent Gram positive human pathogen that is able to form biofilms (Frank et al., *Antimicrob. Agents Chemother.*, 51:888-895 (2007)). As described herein, a polypeptide obtained from *S. lugdunensis* can have glycosyl hydrolase activity and can be used as a biofilm-releasing enzyme to treat or prevent a range of biofilm-associated bacterial infections.

In general, one aspect of this document features an isolated nucleic acid molecule that encodes a polypeptide having a length of at least 300 amino acid residues and at least about 95 percent identity to the amino acid sequence set forth in SEQ ID NO:2 over the length. The polypeptide can comprise a glycosyl hydrolase activity. The isolated nucleic acid molecule can comprise the nucleic acid sequence set forth in SEQ ID NO:1.

In another aspect, this document features an isolated nucleic acid molecule comprising at least 15 nucleotides in length, wherein the isolated nucleic acid molecule hybridizes under hybridization conditions to the sense or antisense strand of the sequence set forth in SEQ ID NO:1. The hybridization conditions can be highly stringent hybridization conditions. The isolated nucleic acid molecule can comprise at least 1000 nucleotides in length. The isolated nucleic acid molecule can comprise the sequence set forth in SEQ ID NO:1.

In another aspect, this document features a cell comprising an isolated nucleic acid molecule that (a) encodes a polypeptide having a length of at least 300 amino acid residues and at least about 95 percent identity to the amino acid sequence set forth in SEQ ID NO:2 over the length, or (b) comprises at least 15 nucleotides in length, wherein the isolated nucleic acid molecule hybridizes under hybridization conditions to the sense or antisense strand of the sequence set forth in SEQ ID NO:1. The cell can be a prokaryotic cell.

In another aspect, this document features a substantially pure polypeptide comprising an amino acid sequence having a length of at least 300 amino acid residues and at least about 95 percent identity to the amino acid sequence set forth in SEQ ID NO:2 over the length. The polypeptide can comprise a glycosyl hydrolase activity. The polypeptide can be encoded by a nucleic acid molecule comprising the nucleic acid sequence set forth in SEQ ID NO:1. The polypeptide can comprise the amino acid sequence set forth in SEQ ID NO:2.

In another aspect, this document features a method for reducing biofilm present on a surface, wherein the method comprises contacting the surface with a polypeptide of claim 10 under conditions wherein the presence of the biofilm on the surface is reduced. The biofilm can comprise pathogenic bacteria. The surface can be a surface of a catheter. The polypeptide can comprise a glycosyl hydrolase activity. The polypeptide can be encoded by a nucleic acid molecule comprising the nucleic acid sequence set forth in SEQ ID NO:1. The polypeptide can comprise the amino acid sequence set forth in SEQ ID NO:2. The presence of the biofilm on the surface can be reduced to below the level of detection after the contacting step.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 4. Inability to detect poly-N-acetylglucosamine in *S. lugdunensis* extracts by immunoblotting. A. Extracts from 24 hours static phase cells grown in TSBgluc1% were immunoblotted with horseradish peroxidase conjugated wheat germ agglutinin, a lectin which binds N-acetylglucosamine. Cells were boiled in 0.5M EDTA, and the supernatants were treated with proteinase K prior to blotting. B. Extracts from 24 hours biofilm cells grown in TSBgluc1% were immunoblotted with an antibody raised against deacetylated PNAG.

FIG. 7 is a listing of a nucleic acid sequence (SEQ ID NO:1) encoding a *S. lugdunensis* polypeptide.

FIG. 8 is a listing of an amino acid sequence of a *S. lugdunensis* polypeptide (SEQ ID NO:2) encoded by the nucleic acid sequence set forth in FIG. 7.

FIG. 9 is a ClustalW alignment and output aligning a *S. lugdunensis* polypeptide (SEQ ID NO:2) and two closely related sequences. Conserved tryptophan residues are highlighted in yellow.

FIG. 10 is a listing of a nucleic acid sequence (SEQ ID NO:5) encoding a *S. lugdunensis* polypeptide. This sequence was obtained from *S. lugdunensis* strain IDRL-5256 and contains six changes as compared to SEQ ID NO:1 (four non-coding substitutions and two that result in amino acid substitutions (S26A and E44D)).

FIG. 11 is a listing of an amino acid sequence of a *S. lugdunensis* polypeptide (SEQ ID NO:6) encoded by the nucleic acid sequence set forth in FIG. 10.

DETAILED DESCRIPTION

Figure 1:
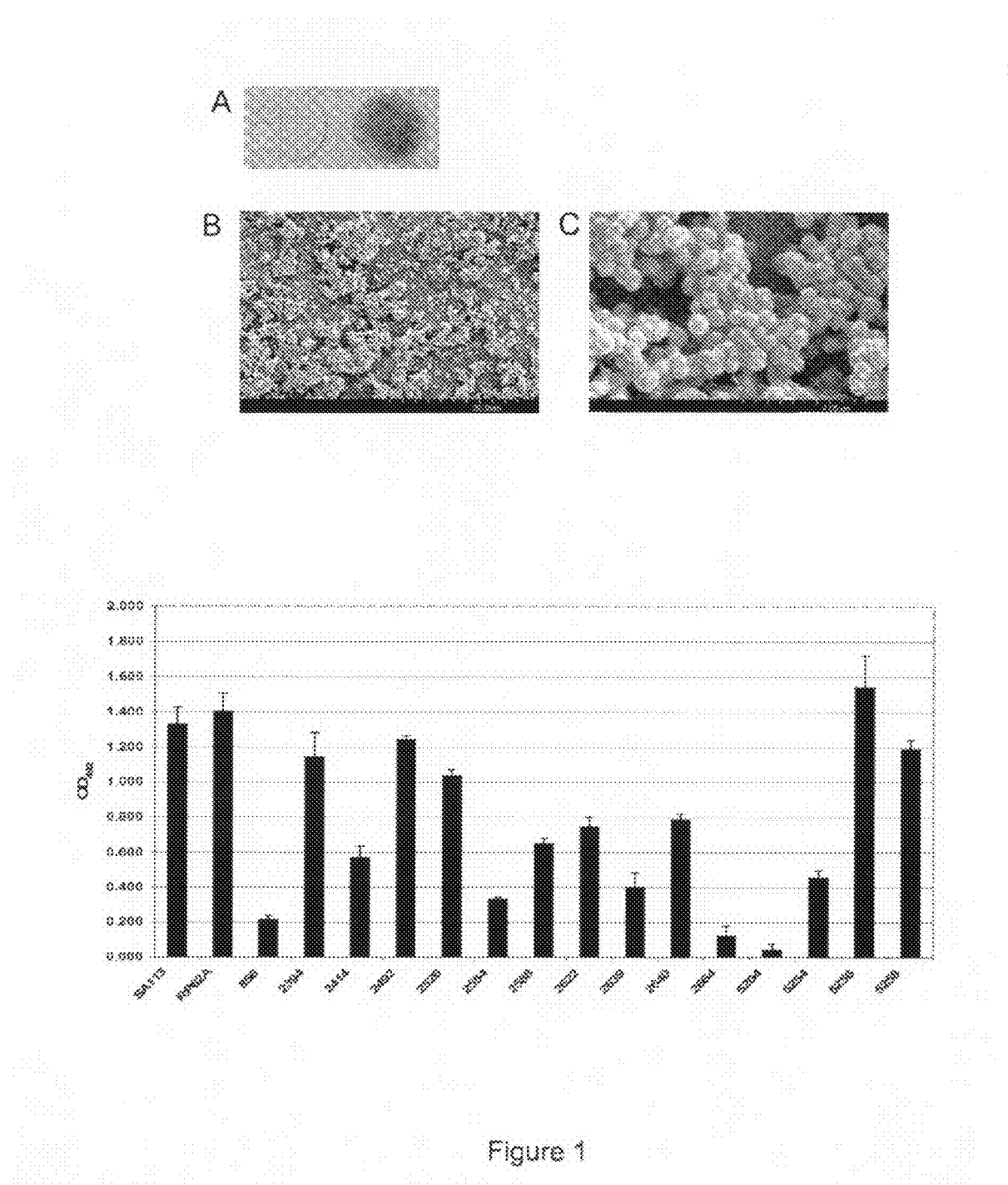
FIG. 1. Characterization of biofilm formation by *S. lugdunensis* clinical isolates. A. *S. lugdunensis* biofilm formation on silicone elastomer. Disks cut from non-reinforced silicone elastomer sheeting were sterilized and incubated for 24 hours in TSBgluc1% (left) or TSBgluc1% containing *S. lugdunensis* IDRL-2640 (right). Disks were rinsed and stained with safranin to visualize biofilms. B. Scanning electron micrograph (1800× magnification) of *S. lugdunensis* IDRL-2640 biofilm formed on silicone elastomer disk after 24 hours. C. Higher magnification (13000×) scanning electron micrograph of biofilm shown in B. D. Biofilm formation of *S. aureus* SA113, *S. epidermidis* RP62A, and 15 clinical *S. lugdunensis* isolates on polystyrene when grown in TSB-gluc1% for 24 hours. Biofilms were stained with safranin, resuspended in 30% glacial acetic acid, and quantified at OD492 nm. Bars are the average of measurements taken from four duplicate wells. Error bars represent the standard deviation. The assay was repeated three times, and representative data from a single replicate is shown.

This document provides isolated nucleic acid molecules, host cells that contain an isolated nucleic acid molecule, and substantially pure polypeptides. In addition, this document provides methods and materials for reducing biofilms, preventing biofilms, and treating infections associated with biofilms.

Nucleic Acids

The term "nucleic acid" as used herein encompasses both RNA and DNA, including cDNA, genomic DNA, and synthetic (e.g., chemically synthesized) DNA. The nucleic acid can be double-stranded or single-stranded. Where single-stranded, the nucleic acid can be the sense strand or the antisense strand. In addition, nucleic acid can be circular or linear.

The term "isolated" as used herein with reference to nucleic acid refers to a naturally-occurring nucleic acid that is not immediately contiguous with both of the sequences with which it is immediately contiguous (one on the 5' end and one on the 3' end) in the naturally-occurring genome of the organism from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" as used herein with reference to nucleic acid also includes any non-naturally-occurring nucleic acid since non-naturally-occurring nucleic acid sequences are not found in nature and do not have immediately contiguous sequences in a naturally-occurring genome. For example, non-naturally-occurring nucleic acid such as an engineered nucleic acid is considered to be isolated nucleic acid. Engineered nucleic acid can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence.

It will be apparent to those of skill in the art that a nucleic acid existing among hundreds to millions of other nucleic acid molecules within, for example, cDNA or genomic libraries, or gel slices containing a genomic DNA restriction digest is not to be considered an isolated nucleic acid.

The term "exogenous" as used herein with reference to nucleic acid and a particular cell refers to any nucleic acid that does not originate from that particular cell as found in nature. Thus, all non-naturally-occurring nucleic acid is considered to be exogenous to a cell once introduced into the cell. It is important to note that non-naturally-occurring nucleic acid can contain nucleic acid sequences or fragments of nucleic acid sequences that are found in nature provided the nucleic acid as a whole does not exist in nature. For example, a nucleic acid molecule containing a genomic DNA sequence within an expression vector is non-naturally-occurring nucleic acid, and thus is exogenous to a cell once introduced into the cell, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid.

Nucleic acid that is naturally-occurring can be exogenous to a particular cell. For example, an entire chromosome isolated from a cell of person X is an exogenous nucleic acid with respect to a cell of person Y once that chromosome is introduced into Y's cell.

This document provides isolated nucleic acid molecules that contain a nucleic acid sequence having (1) a length, and (2) a percent identity to an identified nucleic acid sequence over that length. This document also provides isolated nucleic acid molecules that contain a nucleic acid sequence encoding a polypeptide that contains an amino acid sequence having (1) a length, and (2) a percent identity to an identified amino acid sequence over that length. Typically, the identified nucleic acid or amino acid sequence is a sequence referenced by a particular sequence identification number, and the nucleic acid or amino acid sequence being compared to the identified sequence is referred to as the target sequence. For example, an identified sequence can be the sequence set forth in SEQ ID NO:1 2, 5, or 6.

A length and percent identity over that length for any nucleic acid or amino acid sequence is determined as follows. First, a nucleic acid or amino acid sequence is compared to the identified nucleic acid or amino acid sequence using the BLAST 2 Sequences (B12seq) program from the stand-alone version of BLASTZ containing BLASTN version 2.0.14 and BLASTP version 2.0.14. This stand-alone version of BLASTZ can be obtained from the State University of New York—Old Westbury campus library as well as at Fish & Richardson's web site (world wide web at "fr.com/blast/") or the U.S. government's National Center for Biotechnology Information web site (world wide web at "ncbi.nlm.nih.gov"). Instructions explaining how to use the B12seq program can be found in the readme file accompanying BLASTZ. B12seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to −1; -r is set to 2; and all other options are left at their default setting. For example, the following command can be used to generate an output file containing a comparison between two sequences: C:\B12seq-i c:\seq1.txt-j c:\seq2.txt-p blastn-o c:\output.txt-q-1-r 2. To compare two amino acid sequences, the options of B12seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\B12seq-i c:\seq1.txt-j c:\seq2.txt-p blastp-o c:\output.txt. If the target sequence shares homology with any portion of the identified sequence, then the designated output file will present those regions of homology as aligned sequences. If the target sequence does not share homology with any portion of the identified sequence, then the designated output file will not present aligned sequences. Once aligned, a length is determined by counting the number of consecutive nucleotides or amino acid residues from the target sequence presented in alignment with sequence from the identified sequence starting with any matched position and ending with any other matched position. A matched position is any position where an identical nucleotide or amino acid residue is presented in both the target and identified sequence. Gaps presented in the target sequence are not counted since gaps are not nucleotides or amino acid residues. Likewise, gaps presented in the identified sequence are not counted since target sequence nucleotides or amino acid residues are counted, not nucleotides or amino acid residues from the identified sequence.

The percent identity over a determined length is determined by counting the number of matched positions over that length and dividing that number by the length followed by multiplying the resulting value by 100. For example, if (1) a 1000 nucleotide target sequence is compared to the sequence set forth in SEQ ID NO:1, (2) the B12seq program presents 200 nucleotides from the target sequence aligned with a region of the sequence set forth in SEQ ID NO:1 where the first and last nucleotides of that 200 nucleotide region are matches, and (3) the number of matches over those 200 aligned nucleotides is 180, then the 1000 nucleotide target sequence contains a length of 200 and a percent identity over that length of 90 (i.e., 180÷200*100=90).

It will be appreciated that a single nucleic acid or amino acid target sequence that aligns with an identified sequence can have many different lengths with each length having its own percent identity. For example, a target sequence containing a 20 nucleotide region that aligns with an identified sequence as follows has many different lengths including those listed in Table 1.

This document provides isolated nucleic acid molecules containing a nucleic acid sequence having a length and a percent identity to the sequence set forth in SEQ ID NO:1 or 5 over that length such that the length is at least about 500 nucleotides (e.g., at least about 500, 600, 700, 800, 900, 1000, 1100, 1200, 1300, 1400, or more nucleotides) and the percent identity is at least about 80 percent (e.g., at least about 80, 85, 90, 95, 96, 97, 98, 99, or 100 percent). For example, an isolated nucleic acid molecule provided herein can contain a length of about 1000 nucleotides (e.g., about 1035 nucleotides) with a 90, 95, 99, or 100 percent identify over that length to the sequence set forth in SEQ ID NO:1.

In some cases, an isolated nucleic acid molecule provided herein can contain the nucleotide sequence set forth in SEQ ID NO:1 or 5 without any nucleotide additions, deletions, or substitutions. In some cases, an isolated nucleic acid molecule provided herein can contain the nucleotide sequence set forth in SEQ ID NO:1 or 5 with one or more nucleotide additions, deletions, or substitutions (e.g., one, two, three, four, five, six, seven, eight, nine, ten, 15, 20, 25, 50, or 100 nucleotide additions, deletions, or substitutions).

This document also provides isolated nucleic acid molecules that are at least about 12 bases in length (e.g., at least about 13, 14, 15, 16, 17, 18, 19, 20, 25, 30, 40, 50, 60, 100, 250, 500, 750, 800, 850, 900, 950, 1000, 1035, 1050, 1100, 1150, 1200, 1250, 1300, 1400, 1500, 2000, 3000, 4000, or 5000 bases in length) and hybridize, under hybridization conditions, to the sense or antisense strand of a nucleic acid having the sequence set forth in SEQ ID NO:1 or 5. The hybridization conditions can be moderately or highly stringent hybridization conditions. Such nucleic acid molecules can be molecules that do not hybridize to the sense or antisense strand of a nucleic acid having the sequence encoding the full amino acid sequence set forth in SEQ ID NO:3 or 4.

For the purpose of this invention, moderately stringent hybridization conditions mean the hybridization is performed at about 42° C. in a hybridization solution containing 25 mM KPO$_4$(pH 7.4), 5×SSC, 5× Denhart's solution, 50 µg/mL denatured, sonicated salmon sperm DNA, 50% formamide, 10% Dextran sulfate, and 1-15 ng/mL probe (about 5×10$^7$ cpm/µg), while the washes are performed at about 50° C. with a wash solution containing 2×SSC and 0.1% sodium dodecyl sulfate.

```
                        1                  20
Target Sequence:        AGGTCGTGTACTGTCAGTCA    (SEQ ID NO: 88)
                        | || ||| |||| ||||| |
Identified Sequence:    ACGTGGTGAACTGCCAGTGA    (SEQ ID NO: 89)
```

TABLE 1

| Starting Position | Ending Position | Length | Matched Positions | Percent Identity |
|---|---|---|---|---|
| 1 | 20 | 20 | 15 | 75.0 |
| 1 | 18 | 18 | 14 | 77.8 |
| 1 | 15 | 15 | 11 | 73.3 |
| 6 | 20 | 15 | 12 | 80.0 |
| 6 | 17 | 12 | 10 | 83.3 |
| 6 | 15 | 10 | 8 | 80.0 |
| 8 | 20 | 13 | 10 | 76.9 |
| 8 | 16 | 9 | 7 | 77.8 |

It is noted that the percent identity value is rounded to the nearest tenth. For example, 78.11, 78.12, 78.13, and 78.14 is rounded down to 78.1, while 78.15, 78.16, 78.17, 78.18, and 78.19 is rounded up to 78.2. It is also noted that the length value will always be an integer.

Highly stringent hybridization conditions mean the hybridization is performed at about 42° C. in a hybridization solution containing 25 mM KPO$_4$(pH 7.4), 5×SSC, 5× Denhart's solution, 50 µg/mL denatured, sonicated salmon sperm DNA, 50% formamide, 10% Dextran sulfate, and 1-15 ng/mL probe (about 5×10$^7$ cpm/µg), while the washes are performed at about 65° C. with a wash solution containing 0.2×SSC and 0.1% sodium dodecyl sulfate.

Isolated nucleic acid molecules provided herein can be obtained using any method including, without limitation, common molecular cloning and chemical nucleic acid synthesis techniques. For example, PCR can be used to obtain an isolated nucleic acid molecule containing a nucleic acid sequence sharing similarity to the sequences set forth in SEQ ID NO:1. PCR refers to a procedure or technique in which target nucleic acid is amplified in a manner similar to that described in U.S. Pat. No. 4,683,195, and subsequent modifications of the procedure described therein. Generally, sequence information from the ends of the region of interest or beyond are used to design oligonucleotide primers that are identical or similar in sequence to opposite strands of a potential template to be amplified. Using PCR, a nucleic acid sequence can be amplified from RNA or DNA. For example, a nucleic acid sequence can be isolated by PCR amplification from total cellular RNA, total genomic DNA, and cDNA as well as from bacteriophage sequences, plasmid sequences, viral sequences, and the like. When using RNA as a source of template, reverse transcriptase can be used to synthesize complimentary DNA strands.

Isolated nucleic acid molecules provided herein also can be obtained by mutagenesis. For example, an isolated nucleic acid containing a sequence set forth in SEQ ID NO:1 can be mutated using common molecular cloning techniques (e.g., site-directed mutagenesis). Possible mutations include, without limitation, deletions, insertions, and substitutions, as well as combinations of deletions, insertions, and substitutions.

In addition, nucleic acid and amino acid databases (e.g., GenBank®) can be used to obtain an isolated nucleic acid molecule provided herein. For example, any nucleic acid sequence having some homology to a sequence set forth in SEQ ID NO:1 or 5, or any amino acid sequence having some homology to a sequence set forth in SEQ ID NO:2 or 6 can be used as a query to search GenBank®.

Further, nucleic acid hybridization techniques can be used to obtain an isolated nucleic acid molecule provided herein. Briefly, any nucleic acid molecule having some homology to a sequence set forth in SEQ ID NO:1 or 5 can be used as a probe to identify a similar nucleic acid by hybridization under conditions of moderate to high stringency. Once identified, the nucleic acid molecule then can be purified, sequenced, and analyzed to determine whether it is a nucleic acid molecule described herein.

Hybridization can be done by Southern or Northern analysis to identify a DNA or RNA sequence, respectively, that hybridizes to a probe. The probe can be labeled with a biotin, digoxygenin, an enzyme, or a radioisotope such as $^{32}P$. The DNA or RNA to be analyzed can be electrophoretically separated on an agarose or polyacrylamide gel, transferred to nitrocellulose, nylon, or other suitable membrane, and hybridized with the probe using standard techniques well known in the art such as those described in sections 7.39-7.52 of Sambrook et al., (1989) Molecular Cloning, second edition, Cold Spring harbor Laboratory, Plainview, N.Y. Typically, a probe is at least about 20 nucleotides in length. For example, a probe corresponding to a 20 nucleotide sequence set forth in SEQ ID NO:1 can be used to identify an identical or similar nucleic acid. In addition, probes longer or shorter than 20 nucleotides can be used.

This document provides isolated nucleic acid molecules that contain the entire nucleic acid sequence set forth in SEQ ID NO:1 or 5. In addition, this document provides isolated nucleic acid molecules that contain a portion of the nucleic acid sequence set forth in SEQ ID NO:1 or 5. For example, this document provides an isolated nucleic acid molecule that contains a 600 nucleotide sequence identical to any 600 nucleotide sequence set forth in SEQ ID NO:1, including, without limitation, the sequence starting at nucleotide number 1 and ending at nucleotide number 600, the sequence starting at nucleotide number 2 and ending at nucleotide number 601, the sequence starting at nucleotide number 3 and ending at nucleotide number 602, and so forth. It will be appreciated that this document also provides isolated nucleic acid molecules that contain a nucleotide sequence that is greater than 600 nucleotides (e.g., 650, 700, 750, 800, 850, 900, 950, 1000, 1035, 1050, 1100, 1150, 1200, or more nucleotides) in length and identical to any portion of the sequence set forth in SEQ ID NO:1. For example, this document provides an isolated nucleic acid molecule that contains a 1000 nucleotide sequence identical to any 800 nucleotide sequence set forth in SEQ ID NO:1 including, without limitation, the sequence starting at nucleotide number 1 and ending at nucleotide number 1000, the sequence starting at nucleotide number 2 and ending at nucleotide number 1001, the sequence starting at nucleotide number 3 and ending at nucleotide number 1002, and so forth. Additional examples include, without limitation, isolated nucleic acid molecules that contain a nucleotide sequence that is 25 or more nucleotides (e.g., 50, 100, 150, 200, 250, 300, 350, or more nucleotides) in length and identical to any portion of the sequence set forth in SEQ ID NO:1.

In addition, this document provides isolated nucleic acid molecules that contain a variation of the nucleic acid sequence set forth in SEQ ID NO:1 or 5. For example, this document provides an isolated nucleic acid molecule containing a nucleic acid sequence set forth in SEQ ID NO:1 that contains a single insertion, a single deletion, a single substitution, multiple insertions, multiple deletions, multiple substitutions, or any combination thereof (e.g., single deletion together with multiple insertions). This document also provides isolated nucleic acid molecules that contain a variant of a portion of the nucleic acid sequence set forth in SEQ ID NO:1 or 5 as described herein.

This document provides isolated nucleic acid molecules that contain a nucleic acid sequence that encodes the entire amino acid sequence set forth in SEQ ID NO:2 or 6. In addition, this document provides isolated nucleic acid molecules that contain a nucleic acid sequence that encodes a portion of the amino acid sequence set forth in SEQ ID NO:2 or 6. For example, this document provides isolated nucleic acid molecules that contain a nucleic acid sequence that encodes a 25 amino acid sequence identical to any 25 amino acid sequence set forth in SEQ ID NO:2 including, without limitation, the sequence starting at amino acid residue number 1 and ending at amino acid residue number 25, the sequence starting at amino acid residue number 2 and ending at amino acid residue number 26, the sequence starting at amino acid residue number 3 and ending at amino acid residue number 27, and so forth. It will be appreciated that this document also provides isolated nucleic acid molecules that contain a nucleic acid sequence that encodes an amino acid sequence that is greater than 25 amino acid residues (e.g., 26, 30, 50, 100, 150, 200, 250, 300, 325, 344, or more amino acid residues) in length and identical to any portion of the sequence set forth in SEQ ID NO:2 or 6. For example, this document provides isolated nucleic acid molecules that contain a nucleic acid sequence that encodes a 150 amino acid sequence identical to any 150 amino acid sequence set forth in SEQ ID NO:2 including, without limitation, the sequence starting at amino acid residue number 1 and ending at amino acid residue number 150, the sequence starting at amino acid residue number 2 and ending at amino acid residue number 151, the sequence starting at amino acid residue number 3 and ending at amino acid residue number 152, and so forth. Additional examples include, without limitation, isolated nucleic acid molecules that contain a nucleic acid sequence that encodes an amino acid sequence that is 300 or more amino acid residues (e.g., 300, 310, 320, 330, 340, 344, or more amino acid residues) in length and identical to any portion of the sequence set forth in SEQ ID NO:2.

In addition, this document provides isolated nucleic acid molecules that contain a nucleic acid sequence that encodes an amino acid sequence having a variation of the amino acid sequence set forth in SEQ ID NO:2 or 6. For example, this document provides isolated nucleic acid molecules containing a nucleic acid sequence encoding an amino acid sequence set forth in SEQ ID NO:2 that contains a single insertion, a single deletion, a single substitution, multiple insertions, multiple deletions, multiple substitutions, or any combination thereof (e.g., single deletion together with multiple insertions). This document also provides isolated nucleic acid molecules containing a nucleic acid sequence encoding an amino acid sequence that contains a variant of a portion of the amino acid sequence set forth in SEQ ID NO:2 or 6 as described herein.

The isolated nucleic acid molecules provided herein can encode a polypeptide having glycosyl hydrolases activity. Any method can be use to determine whether or not a particular nucleic acid molecule encodes a polypeptide having glycosyl hydrolase activity. For example, cells transfected with a particular nucleic acid molecule can be used to determine whether the expressed polypeptide has glycosyl hydrolase activity.

Polypeptides

This document provides substantially pure polypeptides. The term "substantially pure" as used herein with reference to a polypeptide means the polypeptide is substantially free of other polypeptides, lipids, carbohydrates, and nucleic acid with which it is naturally associated. Thus, a substantially pure polypeptide is any polypeptide that is removed from its natural environment and is at least 60 percent pure. A substantially pure polypeptide can be at least about 65, 70, 75, 80, 85, 90, 95, or 99 percent pure. Typically, a substantially pure polypeptide will yield a single major band on a non-reducing polyacrylamide gel.

A substantially pure polypeptide provided herein can have an amino acid sequence encoded by a nucleic acid molecule provided herein. In some cases, a substantially pure polypeptide provided herein can contain an amino acid sequence having a length and a percent identity to the sequence set forth in SEQ ID NO:2 or 6 over that length as determined herein provided the length is at least about 250 amino acid residues (e.g., at least about 260, 270, 280, 290, 300, 310, 320, 330, 340, 344, or more amino acid residues) and the percent identity is at least about 80 percent (e.g., at least about 80, 85, 90, 95, 96, 97, 98, 99, or 100 percent). For example, a substantially pure polypeptide provided herein can have an amino acid sequence that contains a length of about 340 amino acid residues (e.g., about 344 amino acid residues) with a 90, 95, 99, or 100 percent identify over that length to the sequence set forth in SEQ ID NO:2 or 6.

Any method can be used to obtain a substantially pure polypeptide. For example, common polypeptide purification techniques such as affinity chromatography and HPLC as well as polypeptide synthesis techniques can be used. In addition, any material can be used as a source to obtain a substantially pure polypeptide. For example, transfected cell cultures or S. lugdunensis cultures can be used as a source material. In addition, tissue culture cells engineered to overexpress a particular polypeptide of interest can be used to obtain substantially pure polypeptide. Further, a polypeptide can be engineered to contain an amino acid sequence that allows the polypeptide to be captured onto an affinity matrix. For example, a tag such as c-myc, hemagglutinin, polyhistidine, or Flag™ tag (Kodak) can be used to aid polypeptide purification. Such tags can be inserted anywhere within the polypeptide including at either the carboxyl or amino termini.

Other fusions that could be useful include enzymes that aid in the detection of the polypeptide, such as alkaline phosphatase.

This document provides polypeptides that contain the entire amino acid sequence set forth in SEQ ID NO:2 or 6. In addition, this document provides polypeptides that contain a portion of the amino acid sequence set forth in SEQ ID NO:2 or 6. For example, this document provides polypeptides that contain a 50 amino acid sequence identical to any 50 amino acid sequence set forth in SEQ ID NO:2 including, without limitation, the sequence starting at amino acid residue number 1 and ending at amino acid residue number 50, the sequence starting at amino acid residue number 2 and ending at amino acid residue number 51, the sequence starting at amino acid residue number 3 and ending at amino acid residue number 52, and so forth. It will be appreciated that this document also provides polypeptides that contain an amino acid sequence that is greater than 50 amino acid residues (e.g., 75, 100, 150, 200, 250, 300, 325, 330, 335, 340, 344, or more amino acid residues) in length and identical to any portion of the sequence set forth in SEQ ID NO:2 or 6. For example, this document provides polypeptides that contain a 300 amino acid sequence identical to any 300 amino acid sequence set forth in SEQ ID NO:2 including, without limitation, the sequence starting at amino acid residue number 1 and ending at amino acid residue number 300, the sequence starting at amino acid residue number 2 and ending at amino acid residue number 301, the sequence starting at amino acid residue number 3 and ending at amino acid residue number 302, and so forth. Additional examples include, without limitation, polypeptides that contain an amino acid sequence that is 300 or more amino acid residues (e.g., 321, 322, 323, 324, 325, or more amino acid residues) in length and identical to any portion of the sequence set forth in SEQ ID NO:2.

In addition, this document provides polypeptides containing an amino acid sequence having a variation of the amino acid sequence set forth in SEQ ID NO:2 or 6. For example, this document provides polypeptides containing an amino acid sequence set forth in SEQ ID NO:2 that contains a single insertion, a single deletion, a single substitution, multiple insertions, multiple deletions, multiple substitutions, or any combination thereof (e.g., single deletion together with multiple insertions). This document also provides polypeptides containing an amino acid sequence that contains a variant of a portion of the amino acid sequence set forth in SEQ ID NO:2 or 6 as described herein.

The substantially pure polypeptides provided herein can have glycosyl hydrolase activity. Any method can be use to determine whether or not a particular polypeptide has glycosyl hydrolase activity. For example, cells expressing a particular polypeptide can be used to determine whether the polypeptide has glycosyl hydrolase activity.

Host Cells

This document also provides host cells such as any cell containing at least one isolated nucleic acid molecule described herein. Such cells can be prokaryotic cells (e.g., *E. coli, S. aureus*, or *S. carnosus*) or eukaryotic cells (e.g., insect cells, mammalian cells, or yeast cells). It is noted that cells containing an isolated nucleic acid molecule provided herein are not required to express a polypeptide. In addition, the isolated nucleic acid molecule can be integrated into the genome of the cell or maintained in an episomal state. Thus, host cells can be stably or transiently transfected with a construct containing an isolated nucleic acid molecule provided herein.

Host cells can contain an exogenous nucleic acid molecule that encodes a polypeptide having glycosyl hydrolase activity. Such host cells can express the encoded polypeptide such that the host cells produce a polypeptide having glycosyl hydrolase activity that can be purified.

Any methods can be used to introduce an isolated nucleic acid molecule into a cell. For example, calcium phosphate precipitation, electroporation, heat shock, lipofection, microinjection, and viral-mediated nucleic acid transfer are common methods that can be used to introduce an isolated nucleic acid molecule into a cell.

Using Polypeptides to Reduce Biofilms

The polypeptides provided herein (e.g., an S. lugdunensis glycosyl hydrolase) can be used to reduce biofilms, prevent biofilms, or treat infections associated with biofilms. The biofilm can be located on any surface including a surface of a foreign object at least partially located in a mammal's body. For example, a polypeptide provided herein such as a polypeptide having the amino acid sequence set forth in SEQ ID NO:2 can be used as a catheter lock agent, wherein a solution containing the polypeptide can be distilled into the lumen of an intravascular catheter during periods of catheter disuse, in order to prevent biofilm formation in the catheter lumen. In some cases, a polypeptide provided herein can be used as an anti-biofilm coating on surfaces of catheters and other medical devices. In some cases, a polypeptide provided herein can be used as a therapeutic to detach pre-formed biofilms from a surface of a medical device. In some cases, a polypeptide provided herein can be used to diagnose S. lugdunensis infections.

The invention will be further described in the following examples, which do not limit the scope of the invention described in the claims.

EXAMPLES

Example 1

Poly-N-acetylglucosamine is not a Major Component of the Extracellular Matrix in Biofilms Formed by icaADBC-Positive Staphylococcus lugdunensis Isolates Microorganisms and Growth Conditions Microorganisms used in this example are listed in Table 1. Bacteria stored at −70° C. were freshly streaked on sheep's blood agar or trypticase soy agar before each replicate experiment. For microtiter plate biofilm formation and detachment assays, immunodetection assays, and confocal microscopy assays (unless stated otherwise), isolated colonies from 16 to 24 hour-old plates were grown in trypticase soy broth (BD BBL, Franklin Lakes, N.J.) supplemented with 1% (w/v) sterile-filtered glucose ($TSB_{gluc1\%}$) with shaking at 130 rpm for 22-24 hours. Unless otherwise noted, all experiments were incubated in ambient air at 37° C.

TABLE 1

Microorganisms.

| Strains | Description | Reference or source |
| --- | --- | --- |
| Staphylococcus epidermidis | | |
| RP62A | ATCC 35984; well-characterized biofilm forming strain; icaADBC and PNAG positive | ATCC |
| CSF41498 | Biofilm forming cerebrospinal fluid isolate; icaADBC and PNAG positive | Conlon et al., J. Bacterial., 184: 4400-4408 (2002) |
| IDRL-2873 | Prosthetic joint infection isolate; icaA positive; used as positive control in Southern blots | Frank et al., J. Clin. Microbiol., 42: 4846-4849 (2004) |
| Staphylococcus aureus | | |
| SA113 | ATCC 35556; well-characterized biofilm forming strain; icaADBC and PNAG positive | ATCC |
| SA113 ica::tet | S. aureus SA113 with inactivated icaADBC locus; deficient for biofilm formation and PNAG production | Cramton et al., Infect. Immun., 67: 5427-5433 (1999) |
| RN4220 | Biofilm-forming strain; icaADBC and PNAG positive (weak) | Kreiswirth et al., Nature, 305: 709-712 (1983) |
| IDRL-2590 | Prosthetic joint infection isolate; icaA positive strain; used as positive control in Southern blots | Frank et al., J. Clin. Microbiol., 42: 4846-4849 (2004) |
| Staphylococcus carnosus | | |
| TM300 | Non-biofilm forming strain; icaADBC and PNAG negative | Gotz et al., Mol. Gen. Genet., 189: 340-342 (1983) |
| TM300 + pCN27 | S. carnosus TM300 carrying plasmid pCN27 containing icaADBC cloned from S. epidermidis RP62A; biofilm and PNAG positive | Heilmann et al., Mol. Microbiol., 20: 1083-1091 (1996) |
| Staphylococcus lugdunensis | | |
| IDRL-856 | Endocarditis isolate | Frank et al., Antimicrob. Agents Chemother., 51: 888-895 (2007) |
| IDRL-2394 | Prosthetic joint infection isolate | Frank et al., Antimicrob. Agents Chemother., 51: 888-895 (2007) |
| IDRL-2414 | Endocarditis isolate | Frank et al., Antimicrob. Agents Chemother., 51: 888-895 (2007) |
| IDRL-2492 | Endocarditis isolate | Frank et al., Antimicrob. Agents Chemother., 51: 888-895 (2007) |
| IDRL-2526 | Prosthetic joint infection isolate | Frank et al., Antimicrob. Agents Chemother., 51: 888-895 (2007) |
| IDRL-2554 | Prosthetic joint infection isolate | Frank et al., Antimicrob. Agents Chemother., 51: 888-895 (2007) |
| IDRL-2588 | Infected hematoma isolate | Frank et al., Antimicrob. Agents Chemother., 51: 888-895 (2007) |
| IDRL-2622 | Prosthetic joint infection isolate | Frank et al., Antimicrob. Agents Chemother., 51: 888-895 (2007) |
| IDRL-2639 | Paronychia isolate | Frank et al., Antimicrob. Agents Chemother., 51: 888-895 (2007) |

TABLE 1-continued

Microorganisms.

| Strains | Description | Reference or source |
|---|---|---|
| IDRL-2640 | Folliculitis isolate | Frank et al., Antimicrob. Agents Chemother., 51: 888-895 (2007) |
| IDRL-2664 | Prosthetic joint infection isolate | Frank et al., Antimicrob. Agents Chemother., 51: 888-895 (2007) |
| IDRL-5204 | Prosthetic joint infection isolate | Frank et al., Antimicrob. Agents Chemother., 51: 888-895 (2007) |
| IDRL-5254 | Intravascular catheter infection isolate | Frank et al., Antimicrob. Agents Chemother., 51: 888-895 (2007) |
| IDRL-5256 | Prosthetic joint infection isolate | Frank et al., Antimicrob. Agents Chemother., 51: 888-895 (2007) |
| IDRL-5258 | Prosthetic joint infection isolate | Frank et al., Antimicrob. Agents Chemother., 51: 888-895 (2007) |
| *Escherichia coli* ATCC 10798 | K-12 strain; used as negative control in Southern blots | ATCC |

Microtiter Plate Biofilm Formation Assay

Biofilm formation was assayed using a microtiter plate assay as described elsewhere (Christensen et al., *J. Clin. Microbiol.*, 22:996-1006 (1985)), with modifications as described elsewhere (Chaignon et al., *Appl. Microbiol. Biotechnol.*, 75(1):125-132 (2007) and Frank and Patel, *Diagn. Microbiol. Infect. Dis.*, 57:355-359 (2007)). Briefly, cultures were adjusted with $TSB_{gluc1\%}$ to match the turbidity of a 1.0 McFarland standard ($\sim$1-2$\times 10^8$ cfu/mL) and diluted 1:50 in $TSB_{gluc1\%}$ or $TSB_{gluc1\%}$ containing various concentrations of sodium chloride (1-5%, w/v) or ethanol (0.5-4%, v/v). For experiments examining the effect of glucose concentration on biofilm formation, bacteria were grown overnight, adjusted to 1.0 McFarland, and diluted in TSB containing the corresponding amount of glucose being tested (0.5-5%, w/v). 200 μL aliquots of each diluted culture were placed into four wells of 96-well microtiter plates (Nuclon Delta, Nalge Nunc International, Rochester, N.Y.), and incubated for 24 hours. Cell growth was measured by reading the $OD_{600\,nm}$ on a microplate reader (Multiskan, Thermo Electron, Waltham, Mass.). Culture media was discarded, and wells were washed twice by fully submerging plates in deionized water to remove non-adherent cells and allowed to air-dry overnight. Biofilms remaining in the wells were stained with 0.1% safranin for 1 minute, rinsed under running tap water to remove excess stain, and air-dried overnight. In order to ensure homogeneity among stained material in the wells, stained biofilms were resuspended in 200 μL of 30 percent glacial acetic acid, and the $OD_{492\,nm}$ was measured. Wells containing uninoculated media served as sterility controls and spectrophotometric blanks. Each condition was assayed three times on separate days with similar results.

Silicone Elastomer Disk Biofilm Formation and Scanning Electron Microscopy (SEM)

Ten mm diameter disks were cut from 0.020-inch thick non-reinforced medical grade silicone elastomer sheeting (Bentec Medical, Woodland, Calif.) with a skin biopsy punch and sterilized by autoclaving. An overnight culture of *S. lugdunensis* IDRL-2640 was adjusted to match the turbidity of a 1.0 McFarland standard ($\sim$1$\times 10^8$ cfu/mL) and diluted 1:50 in $TSB_{gluc1\%}$. One mL aliquots of the diluted culture or sterile media were added to wells of a 24-well plate (Falcon; BD Biosciences, Franklin Lakes, N.J.). Disks were placed in the bottoms of wells with sterile forceps and incubated for 24 hours at 37° C. in 5% $CO_2$ to allow for biofilm formation. Following incubation, disks were removed from wells, soaked for 5 minutes in 1 mL of sterile phosphate-buffered saline (PBS) to remove planktonic bacteria, and stained with 1 mL 0.1% safranin for 1 minute. Excess stain was removed by repeatedly dipping each disk in sterile water.

To visualize biofilms by electron microscopy, disks were incubated as described above, soaked in 1 mL of sterile water for 5 minute, and placed into Trumps fixative (4% formaldehyde and 1% glutaraldehyde in phosphate buffer, pH 7.3). Following critical-point drying and gold-palladium sputter-coating, disks were imaged by cold field-emission SEM using a Hitachi S-4700 instrument (Hitachi Ltd., Tokyo, Japan).

DNA Extraction

Genomic DNA used for Southern blotting and restriction site PCR was prepared from *S. lugdunensis* isolates, *S. aureus* IDRL-2590, *S. epidermidis* IDRL-2873, and *Escherichia coli* ATCC 10798. *S. aureus* IDRL-2590 and *S. epidermidis* IDRL-2873, used as positive controls in Southern blots, are prosthetic joint infection isolates previously determined to be icaA positive by PCR (Frank et al., *J. Clin. Microbiol.*, 42:4846-4849 (2004)). *E. coli* ATCC 10798 served as a negative control in Southern blots. A single colony of each organism was grown overnight in 200 mL TSB at 37° C. in 5% $CO_2$. Cells were pelleted, resuspended in 4 ml of 200 μg/mL lysostaphin (Sigma-Aldrich, Saint Louis, Mo.), and incubated at 37° C. for 30 minutes. An equal volume of DNA Stat-60 reagent (Tel-test, Inc., Friendswood, Tex.) was added, and cells were mixed by inversion and incubated for 20 minutes at room temperature to facilitate complete lysis prior to DNA extraction and precipitation as recommended by the manufacturer.

Low Stringency icaA and icaR Southern Blots

Genomic DNA ($\sim$5 μg) was digested with restriction enzymes EcoRI (Roche Applied Science, Indianapolis, Ind.) or HaeIII (Invitrogen, Corp., Carlsbad, Calif.), as recommended by the manufacturer, separated by electrophoresis on a 1% agarose gel, and transferred to a nylon membrane by downward capillary transfer (Nytran SuperCharge Turboblotter Kit, Whatman, Inc., Florham Park, N.J.). Southern blotting and washes were performed under low stringency conditions with DIG EasyHyb hybridization solution and the DIG Wash and Block Buffer Set (Roche Applied Science) following the protocol described by the manufacturer for filter hybridization applications. DIG-labeled icaA probes were generated by PCR with the PCR DIG Probe Synthesis Kit (Roche Applied Science) from *S. aureus* IDRL-2590 and *S. epidermidis* IDRL-2873 DNA using primers KFicaAF and KFicaAR (Table 2). DIG-labeled icaR probes were generated from *S. aureus* and *S. epidermidis* DNA with primer pairs SAicaRF/SAicaRR and SEicaRF/SEicaRR, respectively. Bound probes were visualized on X-ray film with the chemiluminescent substrate CSPD (Roche Applied Science) following immunological detection with an alkaline phosphatase-labeled anti-DIG antibody (Roche Applied Science).

TABLE 2

Oligonucleotides.

| Oligo-nucleotide name | Sequence | SEQ ID NO: |
|---|---|---|
| icaAR | 5'-CCTCTGTCTGGGCTTGACC-3' | 7 |
| KFicaAF | 5'-GATGGAAGTTCTGATAATAC-3' | 8 |
| KFicaAR | 5'-GTGAAAACACCTGAAATAGTATTGA-3' | 9 |
| SAicaRF | 5'-TTGAAGGATAAGATTATTGATAAC-3' | 10 |
| SAicaRR | 5'-TAGTAGCGAATACACTTCATC-3' | 11 |
| SEicaRF | 5'-TTGAAAGATAAGATTATTGATAAC-3' | 12 |
| SEicaRR | 5'-CATTTAACAGTGAATATACTTG-3' | 13 |
| mRS-BamHI | 5'-GGTACCTAATACGACTCACTATANNNNNNNNNNGGATCC-3' | 14 |
| mRS-EcoRI | 5'-GGTACCTAATACGACTCACTATANNNNNNNNNNGAATTC-3' | 15 |
| mRS-Sau3AI | 5'-GGTACCTAATACGACTCACTATANNNNNNNNNNGATC-3' | 16 |
| mRS-TaqI | 5'-GGTACCTAATACGACTCACTATANNNNNNNNNNTCGA-3' | 17 |
| KLF3F | 5'-CAAAAAAACCAAGGGTAAAG-3' | 18 |
| KLF4R | 5'-ACCTAAAATAGACTTCTTATTTC-3' | 19 |
| KLF5R | 5'-CCCATCACTAGATCATATTGT-3' | 20 |
| KLF6F | 5'-ATGTTAGAACATTTATCGAT-3' | 21 |
| KLF6R | 5'-ATCGATAAATGTTCTAACAT-3' | 22 |
| KLF7F | 5'-AATCCGAAATTGGCTGCGGTA-3' | 23 |
| KLF8F | 5'-TTTAACGAGGAAGAGACGATT-3' | 24 |
| KLF9R | 5'-GAATCAGAACTTCTTGCCCA-3' | 25 |
| KLF11R | 5'-TATTTGGAAACTCTAACGATA-3' | 26 |
| KLF12F | 5'-AGCCACGCGCATTATGTCGAA-3' | 27 |
| KLF13F | 5'-TGCTTGTTCCTGAGACGATAC-3' | 28 |
| KLF14R | 5'-TCGTCTCTTCCTCGTTAAAACA-3' | 29 |
| KLF15R | 5'-ATTAAAAAGGAAATACCT-3' | 30 |
| KLF16F | 5'-AACGTCTTCGATGGGCACAAGG-3' | 31 |
| KLF17F | 5'-CAGCAAAGCACACATTCGTTAGC-3' | 32 |
| KLF18R | 5'-GTCGCAAACGCTCCTTTTTTAC-3' | 33 |
| KLF20F | 5'-GAAAAGAAACACATATTGAT-3' | 34 |
| KLF21R | 5'-GCGGGTCTTTACGCATATTA-3' | 35 |
| KLF22F | 5'-GGCTGTTAAATGCTTTGGTCG-3' | 36 |
| KLF25F | 5'-TTACTCCATAAACATCATCC-3' | 37 |
| KLF26R | 5'-GTTGAAAATCAAGCATTGT-3' | 38 |
| KLF27R | 5'-CATAGCTAGAAACAACCTGTC-3' | 39 |
| KLF28F | 5'-CAATTTGTTATTGCGCTATTC-3' | 40 |
| KLF29R | 5'-TACCTTTGACGTTGAGCG-3' | 41 |
| KLF31F | 5'-CACATACCATTTCTAGTGC-3' | 42 |
| KLF32F | 5'-TGCCGTTTGTCTTGTACTTC-3' | 43 |
| KLF33R | 5'-ATTGATTAACTGACGAGATAC-3' | 44 |
| KLF34R | 5'-ATTTTCCATCTATATCTCAC-3' | 45 |
| KLF35R | 5'-GTTTACATTTTCAATATATAG-3' | 46 |
| KLF37R | 5'-TCCTTTTTCTGTTAAAAAATG-3' | 47 |
| KLF38F | 5'-GGTATTAATCATGGCAAAGTTT-3' | 48 |
| KLF43F | 5'-TATCAATAGTTGAATCGTATA-3' | 49 |
| KLF45F | 5'-AATGGCTTAAAGCACATGGGG-3' | 50 |
| KLF46F | 5'-GTAAAGAAGCGTTTGAGGCTG-3' | 51 |
| KLF47R | 5'-GTACTTTTATATTTTGATTGC-3' | 52 |
| KLF48F | 5'-GAAGGGATTCGCTATGGC-3' | 53 |
| KLF49R | 5'-AATATAGCACAATAAGGA-3' | 54 |
| KLF50F | 5'-TGTCATGCTGTGTGTTATTAT-3' | 55 |
| KLF51F | 5'-CAAGCACATCATTGTATTCCG-3' | 56 |
| KLF52R | 5'-ACCTAATTTACGCGATTCACTG-3' | 57 |
| KLF53F | 5'-CGTTTTAAATACATTATTTTG-3' | 58 |
| KLF54F | 5'-TTATTTATGTGTCGGTTGTTTC-3' | 59 |
| KLF56R | 5'-TTACATAGGAGGACCTCTAAG-3' | 60 |
| KLF57F | 5'-GTGATTACATCTGTCATTGCG-3' | 61 |
| KLF57R | 5'-CGCAATGACAGATGTAATCAC-3' | 62 |
| KLF58R | 5'-TGTGCTTGTGATACAGCGTG-3' | 63 |
| KLF59F | 5'-TATGCTTCATTACGCATCACC-3' | 64 |
| KLF60F | 5'-TATTTGAAAGCACGATTAC-3' | 65 |
| KLF60R | 5'-GTAATCGTGCTTTCCAAATA-3' | 66 |
| KLF62R | 5'-TGTCTAACGAAGATGCAGGAC-3' | 67 |
| KLF64F | 5'-TTCATATTCTGCAATAGCCTG-3' | 68 |
| KLF65R | 5'-GTTGCGCATGTGTCGATATC-3' | 69 |
| KLF66F | 5'-GGTGGCTATATTGGTTATAAC-3' | 70 |
| KLF67R | 5'-ATGTTCCTTTAAAATCAAT-3' | 71 |
| KLF68F | 5'-TTGGCATTGGTATTATTTTAC-3' | 72 |
| KLF69F | 5'-GAATTCTATATTTGCCGCT-3' | 73 |
| KLF70F | 5'-CAACCTGCGATGCGTGTTTAAT-3' | 74 |
| KLF70R | 5'-ATTAAACACGCATCGCAGGTTG-3' | 75 |
| KLF71F | 5'-CTGTTGTTGGAACGCTAGGTA-3' | 76 |
| KLF72F | 5'-TTAGGGGACAGCTTCAGGCCA-3' | 77 |
| KLF73F | 5'-TTATTTTTATGTTTGACTTT-3' | 78 |

TABLE 2-continued

Oligonucleotides.

| Oligo-nucleotide name | Sequence | SEQ ID NO: |
|---|---|---|
| KLF73R | 5'-AAAGTCAAACATAAAAATAA-3' | 79 |
| KLF75R | 5'-GTTATTGATGCACGTCTTGG-3' | 80 |
| KLF76F | 5'-ACGAAAATAAACAGTGTCT-3' | 81 |
| KLF76R | 5'-AAGACACTGTTTATTTTCGT-3' | 82 |
| KLF77F | 5'-TCGGAATCATTAATTTGAGAT-3' | 83 |
| KLF78F | 5'-TAACTTTATTAATATAGATGA-3' | 84 |
| KLF79F | 5'-AGGTCAAACGTCTACCC-3' | 85 |
| KLF80R | 5'-AAAAGTCAGTTGGCGATG-3' | 86 |
| KLF82R | 5'-AATGATATTGAAATACAGCG-3' | 87 |

*S. lugdunensis* ica Operon Sequence Acquisition by Restriction Site PCR

Primers KFicaAF and icaAR, which were designed from regions of high homology between the icaA genes of *S. aureus* and *S. epidermidis* and were reportedly used to amplify icaA from a *S. lugdunensis* isolate causing ventriculoperitoneal shunt infection (Sandoe et al., *Clin. Microbiol. Infect.*, 7:385-387 (2001)), were used in standard PCR reactions with *S. lugdunensis* genomic DNA. PCR was performed using AmpliTaq Gold with Buffer I (Applied Biosystems, Foster City, Calif.) under low stringency annealing conditions (42° C.). The resulting PCR products were sequenced with the same primers. Restriction-site PCR (Sarkar et al., *PCR Methods Appl.*, 2:318-322 (1993)), a primer walking strategy that couples outward facing primers of known sequence with a universal primer that recognizes a specific restriction enzyme recognition site, was used to acquire the sequence of the entire region encompassing the icaADBC locus from *S. lugdunensis* IDRL-2414 and IDRL-2664. Outward facing primers that annealed to the 5' and 3' regions of the initial *S. lugdunensis* icaA sequence were paired in standard PCR reactions with one of four restriction-site PCR primers, mRS-BamHI, mRS-EcoRI, mRS-Sau3AI, or mRS-TaqI (Table 2). One microliter of the first reaction was used as the template in a second PCR reaction containing a primer located internal to the first round primer and the restriction-site PCR primer used in the first round. Resulting products were analyzed by gel electrophoresis and sequenced with the second round specific primer. All sequence was verified bi-directionally. Table 2 lists primers used for restriction-site PCR or bi-directional sequence verification. Sequencing was performed on an ABI Prism 377 DNA sequencer with an ABI Prism Big Dye Terminator cycle sequencing ready reaction kit (Perkin-Elmer Applied Biosciences, Foster City, Calif.) at the Mayo Clinic DNA Sequencing core facility. Primers were synthesized by the Mayo Clinic DNA Synthesis core facility or Integrated DNA Technologies, Inc. (Coralville, Iowa).

*S. lugdunensis* ica Locus PCR Screen

Primer pairs KLF64F/KLF82R and KLF32F/KLF67R (Table 2) were used to PCR amplify 7.6 kb and 4.9 kb products, respectively, from the region spanning the *S. lugdunensis* icaADBC locus. PCR was performed with Platinum PCR SuperMix High Fidelity (Invitrogen) using template DNA prepared by alkaline wash, as described elsewhere (Frank et al., *J. Clin. Microbiol.*, 42:4846-4849 (2004)). *S. lugdunensis* IDRL-2414, IDRL-2664, IDRL-5204, IDRL-5256, and IDRL-5258 PCR products were bi-directionally sequenced. Sequencing primers are listed in Table 2. Sequence alignments and comparisons were performed with Sequencher software (Gene Codes Corp., Ann Arbor, Mich.).

Immunoblot Detection of PNAG and Other Polysaccharides in Static Phase or Biofilm *S. lugdunensis* Cells The production of PNAG was assessed as previously elsewhere (Cramton et al., *Infect. Immun.*, 67:5427-5433 (1999)), with some modifications. For static phase cells, bacteria were grown overnight in $TSB_{gluc1\%}$, and equivalent amounts (1-2 mL) of cells, as determined by optical density, were harvested. For biofilm cells, biofilms were established as described above in 48 well microtiter plates (Nuclon Delta, Nalge Nunc International) containing 500 µL of culture. Biofilms from two wells per organism were scraped with a pipette tip, resuspended in the culture media, and pooled. Cell pellets were washed in sterile PBS, resuspended in 0.5 M EDTA, sonicated for 5 minutes at 40 kHz in a bath sonicator (Zenith Ultrasonics, Norwood, N.J.), boiled 5 minutes, and centrifuged. Supernatants were treated with 200 µg proteinase K for 30 minutes at 65° C., then 80° C. for 15 minutes to heat inactivate the enzyme. Extracts were spotted onto nitrocellulose, and blots were blocked 1 hour in 3% bovine serum albumin (BSA) in tris-buffered saline (TBS). Blots were probed overnight at 4° C. with a 1:5,000 dilution of goat anti-deacetylated PNAG antibody (Maira-Litran et al., *Infect. Immun.*, 73:6752-6762 (2005)) in TBS-0.05% Tween-20 with 3% BSA. The anti-deacetylated PNAG antibody was obtained from Jerry Pier at Harvard Medical School. Blots were washed and probed with a 1:10,000 dilution of rabbit anti-goat horseradish peroxidase conjugate (Pierce, Rockford, Ill.) in TBS-0.05% Tween-20 with 3% skim milk for 1-4 hours at room temperature. Alternatively, blots were probed with wheat germ agglutinin horseradish peroxidase conjugate (Sigma Aldrich), as described elsewhere (Jefferson and Cerca, Bacterial-bacterial cell interactions in biofilms: detection of polysaccharide intercellular adhesins by blotting and confocal microscopy, p. 119-126. In S. P. Colgan (ed.), Methods Mol. Biol., vol. 341. (2006) Humana Press, Totowa). Bound probes were visualized on X-ray film with the chemiluminesence ECL kit (Amersham Biosciences, Pittsburgh, Pa.).

The biotinylated lectin screening kit-I (Vector Laboratories, Burlingame, Calif.) was used to screen blots for the presence of other polysaccharides released from static phase cells. Blots were blocked at room temperature for at least 1 hour in TBS-0.1% Tween-20 with or without 5% BSA, depending on optimized conditions for individual lectins, followed by 1 hour incubation at room temperature with 5 µg/mL lectin in TBS-0.1% Tween-20. Bound lectins were detected with the Vectastain Elite ABC kit (Vector Laboratories), as recommended by the manufacturer for the use of biotinylated lectins in Western blotting applications, and visualized on X-ray film with the ECL kit.

Scanned film images were adjusted with the brightness and contrast functions in Microsoft Office Picture Manager software.

Microtiter Plate Biofilm Detachment Assay 40 mM sodium metaperiodate ($NaIO_4$, Sigma-Aldrich) in water, 40 µg/mL purified recombinant dispersin B (obtained from Kane Biotech Inc., Winnipeg, Manitoba, Canada) in sodium phosphate buffer (50 mM sodium phosphate (pH 5.8), 100 mM NaCl), 100 µg/mL proteinase K (Roche Applied Science) in 10 mM Tris-HCl pH 7.5, 10 U/mL trypsin (Promega Corp., Madison, Wis.) in 10 mM Tris-HCl pH 7.5, 100 µg/mL chymotrypsin (Sigma-Aldrich) in 10 mM Tris- HCl pH 7.5, and 100 µg/mL thermolysin (Sigma-Aldrich) in 10 mM Tris-HCl pH 7.5 were tested for their ability to detach pre-formed *S. lugdunensis* biofilms from polystyrene microtiter plate wells. For certain experiments, proteinase K was inactivated by boiling for 40 minutes.

Biofilms grown in $TSB_{gluc1\%}$ were formed in wells of microtiter plates and washed twice with deionized water, as described above for the microtiter plate biofilm formation assay. 100 µL of $NaIO_4$, enzyme, or suitable control was carefully added so as not to mechanically detach biofilms on the bottoms of wells. Plates were incubated at 37° C. for 2 hours, and contents of wells were discarded and washed twice with deionized water. Plates were air-dried overnight, stained with 0.1% safranin for 1 minute, and processed as described above to quantify the amount of stained biofilm remaining after treatment, relative to treatment with the control reagent. Four wells were measured for each treatment condition. Assays were repeated two or three times on separate days with similar results.

Confocal Scanning Laser Microscopy (CSLM)

Biofilms were grown for microscopy in 4-well chambered coverglass (Lab-Tek II, Nalge Nunc International). Overnight cultures were adjusted and diluted 1:50 with $TSB_{gluc1\%}$ as described above for the microtiter plate biofilm formation assay. One mL aliquots were added to chamber wells and statically incubated for 20-24 hours. Media was removed from wells, biofilms were rinsed with 1 mL PBS, and stained for fluorescent CSLM. To visualize PNAG among biofilm cells, biofilms were incubated in the dark for 15 minutes with 1 mL PBS containing 0.09 mg/mL wheat germ agglutinin-Oregon Green 488 conjugate (Molecular Probes, Eugene, Oreg.) and 5 µg/mL FM 4-64 (Molecular Probes), a lipophilic styryl membrane dye used previously to image bacterial cell membranes (Sharp and Pogliano, *Proc. Natl. Acad. Sci. U.S.A.*, 96:14553-14558 (1999)). Stains were removed and wells were rinsed with 2 mL PBS before imaging. Extracellular proteins among biofilm cells were visualized by incubating in the dark for 30 minutes with 1 mL undiluted SYPRO Ruby protein gel stain (Molecular Probes) containing 0.167 µM Syto-9 nucleic acid stain (Molecular Probes). Stains were removed before imaging.

Confocal images were acquired on an LSM510 equipped with an Axiovert 100M inverted microscope using a Plan-Apochromat 100X/1.4 NA oil immersion objective (Carl Zeiss, Inc., Thornwood, N.Y.). An argon laser was used to excite the fluorophores at the following wavelengths: 458 nm for SYPRO Ruby; 488 nm for Oregon Green (wheat germ agglutinin), FM 4-64, and Syto-9. Red fluorescence from SYPRO Ruby and FM 4-64 was detected with a LP 650 filter. Green fluorescence was detected from Oregon Green with a BP 505-550 filter and from Syto-9 with a BP 505-530 filter. Microscopy was performed on at least three different days. Images were prepared with the LSM510 software. Red/green fluorescence ratios to assess biofilm protein were calculated on SYPRO Ruby/Syto-9 images with KS 400 version 3.0 software (Carl Zeiss, Inc.). The fluorescence area (in pixel) was averaged for images taken in two areas per biofilm from two independent biofilms.

Statistical Analysis

Data were analyzed with the Student's t-test using JMP 6.0.0 Software (SAS Institute, Inc., Cary, N.C.).

Nucleotide Sequence Accession Numbers

Accession numbers for complete *S. lugdunensis* icaADBC operon sequences that are in GenBank®, National Center for Biotechnology Information, are: *S. lugdunensis* isolate IDRL-2414, EF546620; *S. lugdunensis* isolate IDRL-2664, EF546621; *S. lugdunensis* isolate IDRL-5204, EF546622; *S. lugdunensis* isolate IDRL-5256, EF546623; and *S. lugdunensis* isolate IDRL-5258, EF546624.

*S. lugdunensis* Clinical Isolates Form Biofilm

The biofilm antimicrobial susceptibility profiles and the effects that subinhibitory antibiotic concentrations elicit on biofilm formation of a collection of *S. lugdunensis* clinical isolates were determined (Frank et al., *Antimicrob. Agents Chemother.*, 51:888-895 (2007)). A majority of the isolates were recovered from infections known to be associated with biofilm etiology, including prosthetic joint infection, endocarditis, and intravascular catheter infection (Table 1). To further characterize *S. lugdunensis* biofilm formation, this collection was evaluated using in vitro biofilm formation assays under growth conditions known to support staphylococcal biofilm formation, namely TSB supplemented with 1% glucose (Deighton et al., *Methods Enzymol.*, 336:177-95 (2001) and Knobloch et al., *Med. Microbiol. Immunol.*, 191: 101-106 (2002)).

*S. lugdunensis* IDRL-2640, a folliculitis isolate, was incubated for 24 hours in $TSB_{gluc1\%}$ with a disk cut from silicone elastomer, a type of material used to manufacture intravascular catheters. Planktonic cells were removed by gentle washing, and the disk was stained with safranin to visualize adherent bacteria. The organism formed a strong confluent layer on the disk (FIG. 1A). SEM visualization of a duplicate disk revealed cells growing in clusters with the development of microcolonies across the disk surface (FIG. 1B). When viewed at higher magnification (FIG. 1C), cells appeared to be organized into a three-dimensional architecture held together by an extracellular polymeric substance. These properties are consistent with organisms growing as a biofilm.

The relative ability of each *S. lugdunensis* isolate to form biofilm was assessed using a polystyrene microtiter plate biofilm formation assay. All isolates were able adhere to polystyrene (FIG. 1D). Compared to the strong biofilm-forming strains *S. aureus* SA113 and *S. epidermidis* RP62A, the biofilm formation phenotype varied widely among the *S. lugdunensis* isolates. In particular, isolates IDRL-2664 and IDRL-5204 were poor biofilm formers, whereas isolates IDRL-2394, IDRL-5256, and IDRL-5258 formed robust biofilms. No correlation between the source of infection (Table 1) and the degree of biofilm formation existed for this set of staphylococci.

*S. lugdunensis* Biofilm Formation is Affected by Environmental Conditions

Figure 2A:
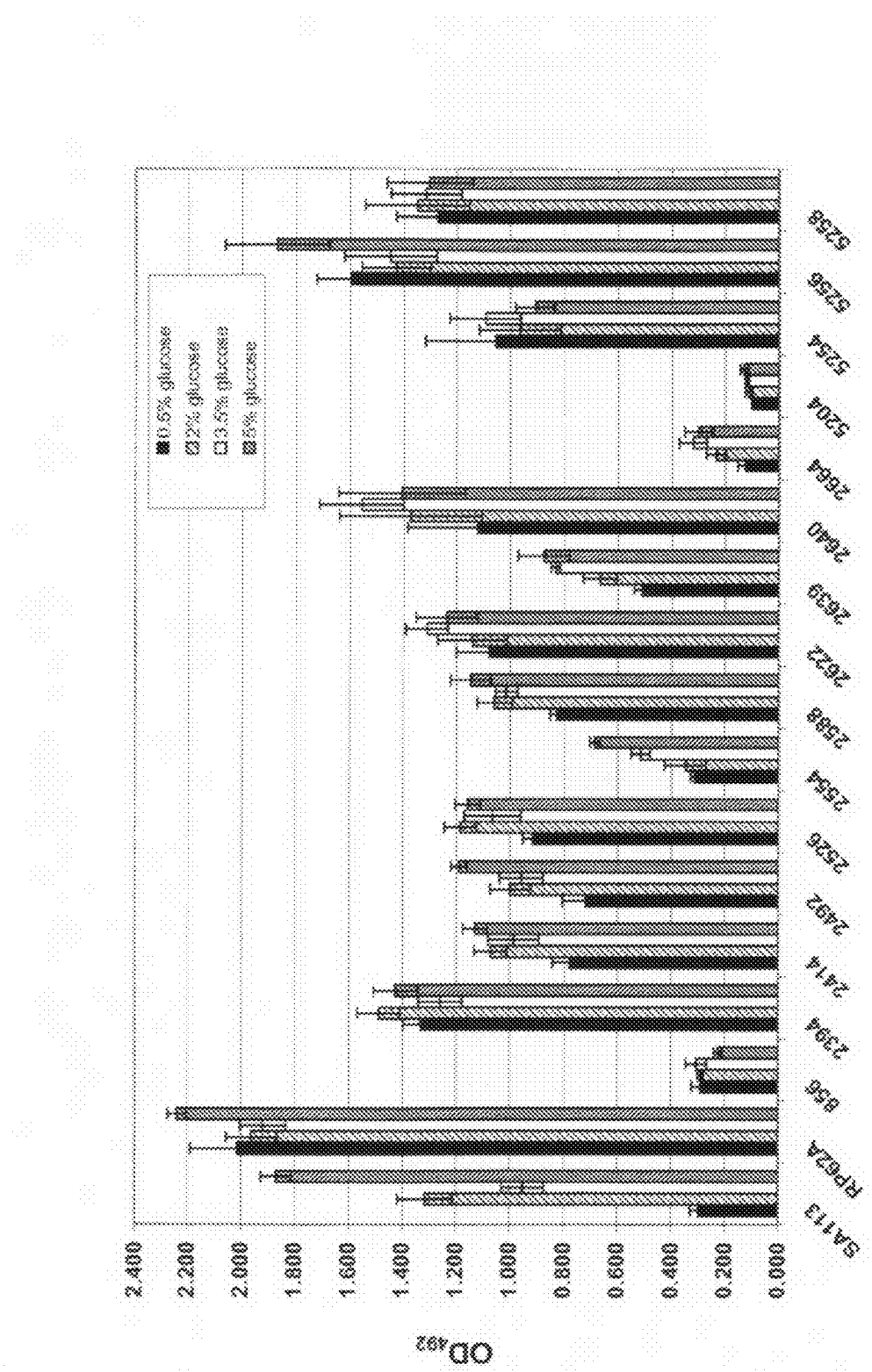
FIG. 2. Effect of environmental factors on *S. lugdunensis* biofilm formation. A. Effect of increasing glucose concentrations on biofilm formation. *S. aureus* SA113, *S. epidermidis* RP62A, and *S. lugdunensis* clinical isolates were grown in wells of polystyrene microtiter plates in TSB supplemented with the indicated concentrations of supplemented glucose. B. *S. lugdunensis* biofilm response to sodium chloride. Organisms were grown in microtiter plates in TSBgluc1% with the indicated concentrations of sodium chloride. C. Biofilm formation in the presence of ethanol. Biofilm formation on polystyrene was assayed after growth in TSBgluc1% containing various concentrations of ethanol. 2% ethanol inhibited growth of *S. lugdunensis* isolates IDRL-2554, IDRL-2640, and IDRL-5254. In each graph, bars are the average biofilm formation of four wells. Error bars represent the standard deviation. Asterisks indicate statistically significant increases or decreases in biofilm formation compared to biofilm formation in the absence (B and C) or the lowest concentration (A) of each environmental factor tested (P-value<0.05, Student's t-test). Data are representative of three replicate experiments with similar results.

Changes in exogenous factors present in growth media that enrich or stress the growth environment, including glucose (Christensen et al., *Infect. Immun.*, 37:318-26 (1982); Dobinsky et al., *J. Bacteriol.*, 185:2879-2886 (2003); and Lim et al., *J. Bacteriol.*, 186:722-729 (2004)), increasing osmolarity (Knobloch et al., *J. Bacteriol.*, 183:2624-2633 (2001); Lim et al., *J. Bacteriol.*, 186:722-729 (2004); and Moretro et al., *Appl. Environ. Microbiol.*, 69:5648-5655 (2003)), and alcohols (Knobloch et al., *J. Antimicrob. Chemother.*, 49:683-7 (2002) and Knobloch et al., *Med. Microbiol. Immunol.*, 191: 101-106 (2002)), influence *S. aureus* and *S. epidermidis* in vitro biofilm formation. The effect of increasing concentrations of glucose, sodium chloride, and ethanol on the collection of *S. lugdunensis* isolates was tested. Statistically measurable increases in biofilm formation in response to heightened glucose levels were observed for *S. aureus* SA113, *S. epidermidis* RP62A, and 80% (12/15) of the *S. lugdunensis* isolates (FIG. 2A). Three *S. lugdunensis* isolates, IDRL-856, IDRL-5254, and IDRL-5258, formed equivalent amounts of biofilm independent of the amount of glucose present in the environment.

Figure 2B:
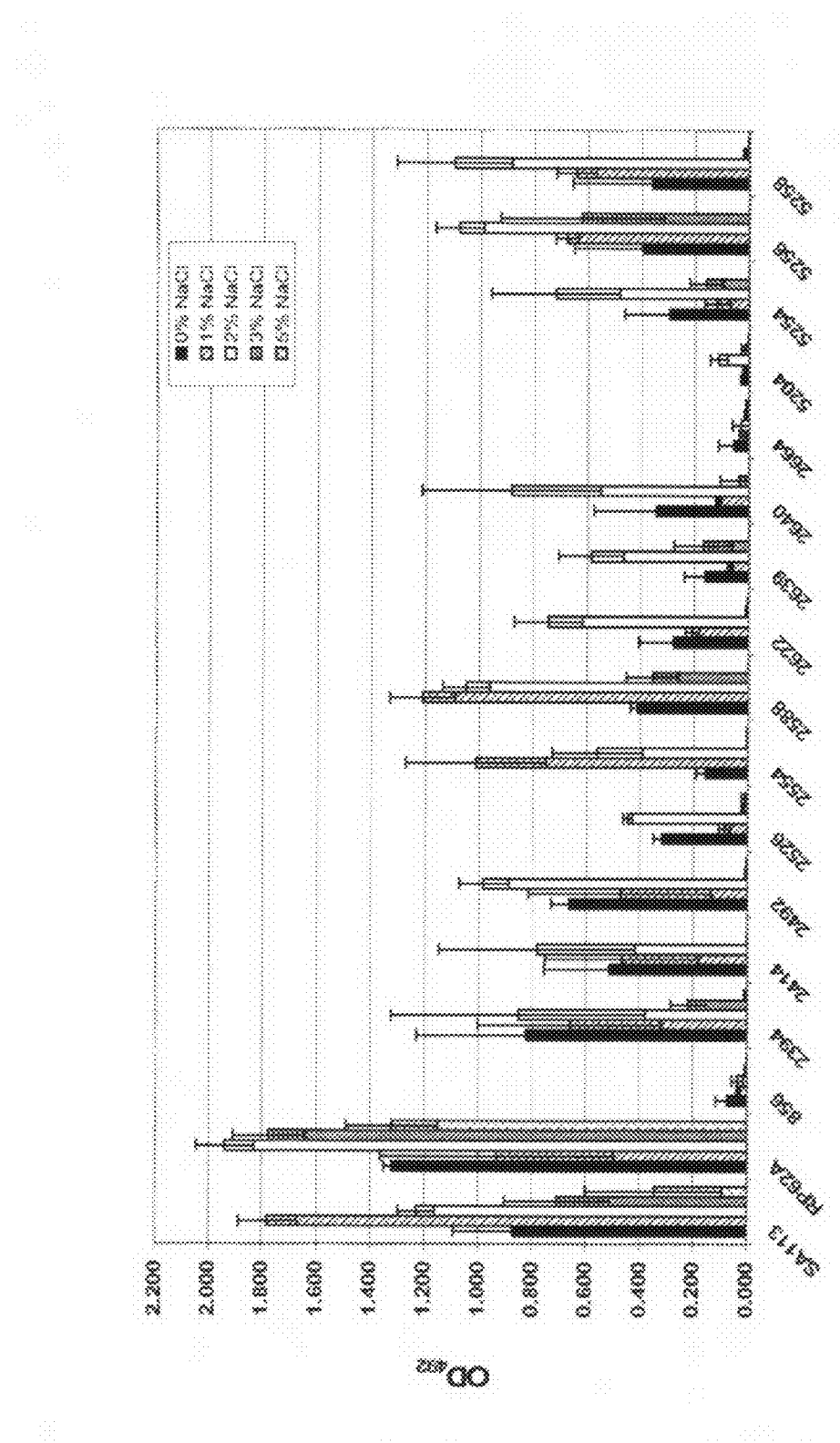

Media enrichment with sodium chloride at concentrations up to 5% (w/v) has been shown to increase microtiter plate biofilm formation in *S. aureus*, *S. epidermidis*, and several other CNS. *S. aureus* SA113 and *S. epidermidis* RP62A biofilm levels were found to increase when grown in $TSB_{gluc1\%}$ with 1-2% or 1-3% sodium chloride, respectively (FIG. 2B). Likewise, 73% (11/15) of the *S. lugdunensis* isolates formed more biofilm in media containing 1 or 2% sodium chloride. In contrast, higher concentrations of salt substantially reduced *S. lugdunensis* adherence to microtiter wells (FIG. 2B). Essentially no measurable quantity of biofilm could be detected when *S. lugdunensis* isolates were incubated with 5% sodium chloride. Compared to baseline biofilm formation, *S. epidermidis* RP62A biofilm was not affected in 5% sodium chloride, whereas the level of *S. aureus* SA113 biofilm was significantly reduced, yet still discernable. Growth of all species tested was not affected by the increasing salt concentrations, as verified by measuring the optical density of the biomass in each well prior to the removal of planktonic cells. These results indicate that high sodium chloride concentrations can directly interfere with the process of *S. lugdunensis* biofilm formation.

Figure 2C:
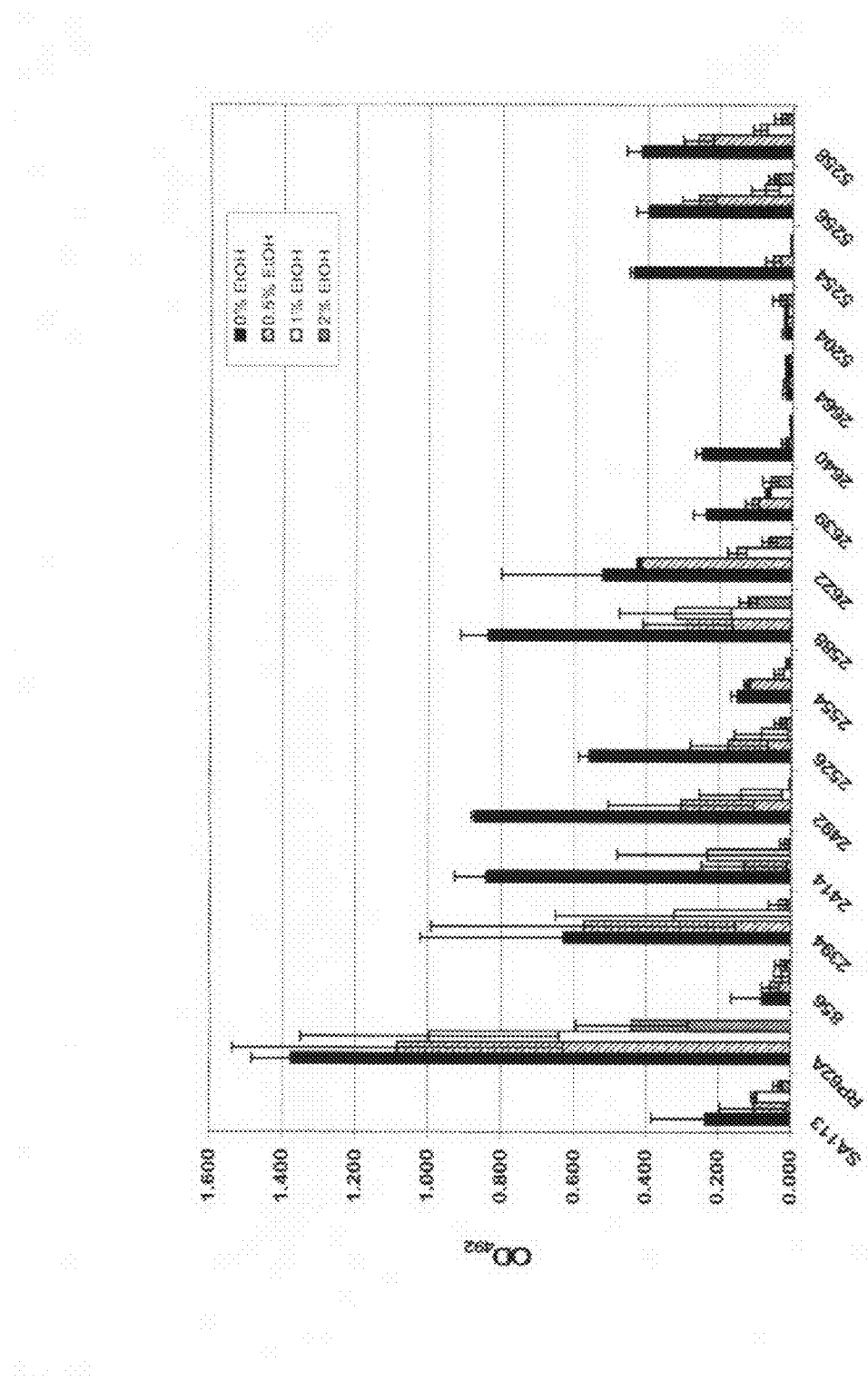

Ethanol concentrations of up to 6% (v/v) are capable of stimulating biofilm formation by clinical *S. epidermidis* isolates (Knobloch et al., *J. Antimicrob. Chemother.*, 49:683-7 (2002)). Positive biofilm-forming *S. aureus* and *S. epidermidis* reference strains both exhibited significant reductions in biofilm production with increasing ethanol concentrations (FIG. 2C). Most ethanol concentrations also reduced the levels of biofilm production of all *S. lugdunensis* isolates that formed biofilm at a baseline level of $OD_{492} \geq 0.150$ nm (FIG. 2C). Not only did 2% ethanol prevent the adherence of all *S. lugdunensis* that formed measurable baseline biofilms, but 4% ethanol was bactericidal for all *S. lugdunensis* isolates. *S. lugdunensis* IDRL-2554, IDRL-2640, and IDRL-5254 were the only isolates killed after incubation in 2% ethanol. These results indicate that *S. lugdunensis* clinical isolates are more susceptible to ethanol than are *S. epidermidis* clinical isolates, and that ethanol appears to be a negative regulator of *S. lugdunensis* biofilm formation.

Identification and Sequencing of icaADBC Homologues in *S. lugdunensis*

In order to determine whether the studied isolates lacked icaA, Southern blots were performed with *S. aureus* and *S. epidermidis* icaA probes under low stringency conditions. Hybridization signals were detected for 100% (n=7) of *S. lugdunensis* prosthetic joint infection isolates tested. This data suggests that the inability to detect icaA in *S. lugdunensis* by PCR might be due to mismatches between primers and the *S. lugdunensis* icaA sequence. Using the primer sequences reported elsewhere (Sandoe et al., *Clin. Microbiol. Infect.*, 7:385-387 (2001)) under low stringency annealing conditions, a short region of an icaA homologue from *S. lugdunensis* was amplified and sequenced. This sequence was extended in both the 5' and 3' directions from *S. lugdunensis* IDRL-2414 and IDRL-2664 using restriction-site PCR, a primer-walking technique developed to acquire unknown sequence surrounding a region of known sequence (Sarkar et al., *PCR Methods Appl.*, 2:318-322 (1993)).

Figure 3:
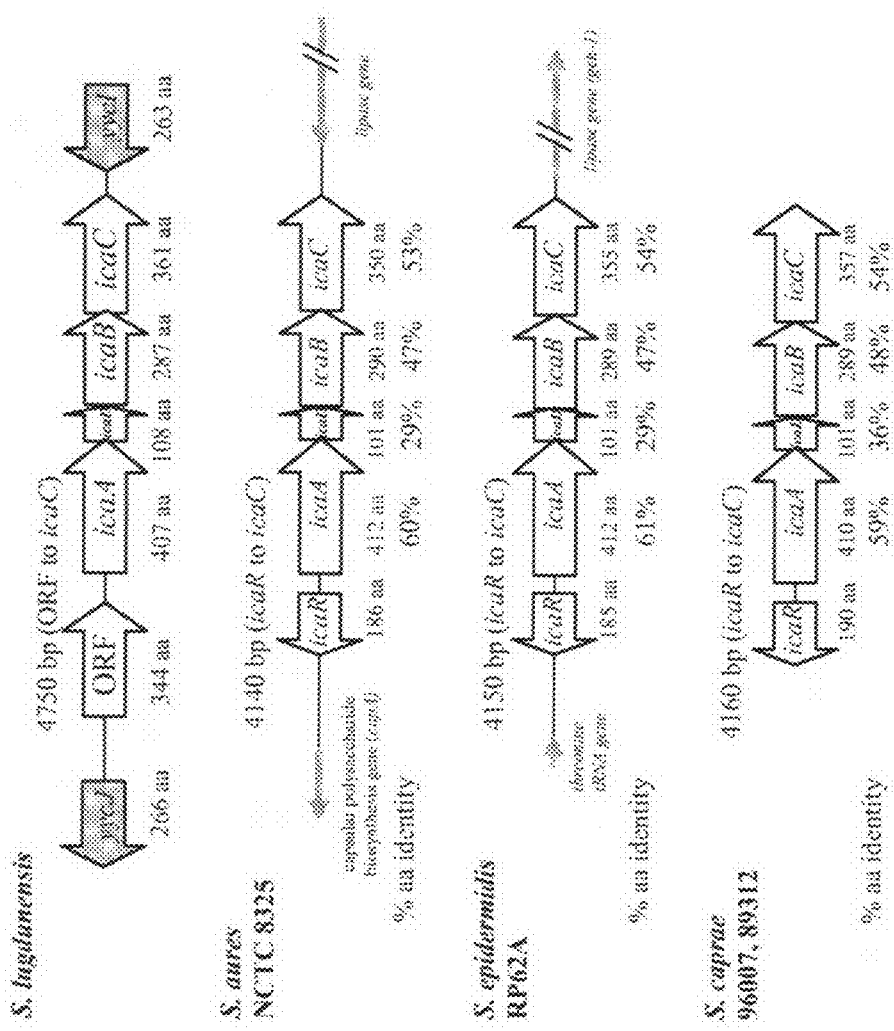
FIG. 3. Genomic organization of the *S. lugdunensis* icaADBC locus. A 7.6 kb chromosomal region encompassing the *S. lugdunensis* icaADBC genes was sequenced from isolates IDRL-2414 and IDRL-2664. An ORF encoding a hypothetical glycosyl hydrolase was found in the position where icaR was expected. The ORF-icaADBC locus was found by PCR to be intact in all *S. lugdunensis* isolates tested in this work. icaADBC loci of *S. epidermidis* RP62A (ATCC 35984, GenBank accession number NC_007795), *S. aureus* NCTC 8325 (GenBank accession number NC_007795), and *S. caprae* strains 96007 (GenBank accession number AF246926) and 89318 (GenBank accession AF246927) are shown for comparison. Percent amino acid identities of *S. lugdunensis* genes with each homologue were determined with ClustalW. Slashes on the lipase genes indicate that they are not drawn to the same scale as the rest of the figure.

A 7.6 kb region of the *S. lugdunensis* genome, which included open reading frames (ORFs) with high degrees of similarity (~30-60% identical at the predicted amino acid level) to icaADBC from *S. aureus*, *S. epidermidis*, and *S. caprae*, were sequenced and annotated (FIG. 3). The predicted amino acid sequences for *S. lugdunensis* IcaA and IcaB are shorter than their homologues in other staphylococci, whereas IcaD and IcaC are longer than their counterparts. icaA overlaps icaD by 31 nucleotides, icaD overlaps icaB by 17 nucleotides, and icaB overlaps icaC by 23 nucleotides. An icaR homologue was not located upstream of icaA, as would be predicted from the conserved genomic organization of the ica loci in *S. aureus*, *S. epidermidis*, and *S. caprae*. Rather, a novel ORF that lacks homology with known staphylococcal sequences was found directly upstream of, and in the same orientation as, icaA. The ORF-icaADBC genes span a 4.75 kb region that includes a 251 nucleotide intergenic region separating the ORF and icaA. Open reading frames with high degrees of similarity to yycJ and yycI genes from *S. aureus* and *S. epidermidis* flanked the ORF-icaADBC region on the 5' and 3' sides, respectively. The finding that yycJ and yycI are separated by greater than 4.7 kb was surprising, as these two genes otherwise occur as part of the YycFG two-component system operon that is highly conserved among Gram positive bacteria.

Inability to Detect icaR in the *S. Lugdunensis* Genome

The absence of icaR upstream of icaA indicated that it might be located elsewhere in the genome of *S. lugdunensis*. No hybridization signals were detected upon low stringency Southern blotting with probes generated from the full-length sequences of icaR from either *S. aureus* or *S. epidermidis*. Low annealing temperature PCR with the primers used to generate the icaR Southern probes from *S. aureus* and *S. epidermidis* was attempted; however, this resulted in non-specific annealing. These results strongly suggest that any icaR homologue would have very little similarity to known icaR sequences from other staphylococci.

A Novel Open Reading Frame with Predicted Glycosyl Hydrolase Activity

The 1,035 nucleotide ORF (FIG. 7) located upstream of the icaA start codon is predicted to encode a 344 amino acid polypeptide (FIG. 8) that is not similar to any currently known staphylococcal sequences as determined by nucleotide and protein BLAST searches SignalP 3.0 analysis of the sequence predicts that the hypothetical polypeptide contains an N-terminal signal sequence between amino acid residues 25 and 26 (Bendtsen et al., *J. Mol. Biol.*, 340:783-795 (2004)). In particular, the ORF is located in the *S. lugdunensis* genome 251 nucleotides upstream of the start codon of the icaADBC locus, and 593 nucleotides downstream of the yycJ gene. The Conserved Domains Database at NCBI's web site was used to identify a putative conserved domain within the predicted ORF amino acid sequence that closely resembles the glycosyl hydrolase family 20 catalytic domain (Accession Number: pfam00728) and a group of N-acetyl-β-hexosaminidases (called Chb; Accession Number: COG3525.2), which are involved in carbohydrate transport and metabolism (Henrissat, *Biochem. J.*, 280 (Pt 2):309-316 (1991)). The substrate binding pocket of family 20 glycosyl hydrolases are lined with several tryptophan residues that create a hydrophobic environment (Tews et al., *Nat. Struct. Biol.*, 3:638-648 (1996)); such tryptophan residues are conserved in the predicted ORF amino acid sequence.

The most closely related translated polypeptide sequences to the translated ORF sequence, as identified in a TBLASTX 2.2.16 search, were the dispersin B (dspB) homologues from *Actinobacillus pleuropneumoniae* and *Actinobacillus actinomycetemcomitans* (Kaplan et al., *J. Bacteriol.*, 185:4693-8 (2003) and Kaplan et al., *J. Bacteriol.*, 186:8213-8220 (2004)). Dispersin B is an N-acetyl-β-hexosaminidase that cleaves the β-1,6-linkages in polymers of N-acetylglucosamine. A ClustalW (World Wide Web at "ebi.ac.uk/clustalw/") comparison indicated that the ORF amino acid sequence is 26% identical to the dispersin B homologues from the two *Actinobacillus* species.

The ORF sequence was cloned, with and without the N-terminal signal sequence, into an *E. coli* overexpression vector (pET-30b). Each plasmid contained its respective ORF sequence (with or without the signal sequence) downstream of a T7 promoter, lac operator, and ribosome binding site, and upstream of sequence that will add a C-terminal thrombin cleavage site and hexa-histidine tag (to facilitate purification with nickel affinity chromatography) to the expressed protein. A brief attempt to induce expression and purify the encoded polypeptide in *E. coli* did not result in detectable polypeptide.

Contribution of ica Locus Sequence Variability to Biofilm Formation Ability

The 7.6 kb genomic region spanning from yycJ through yycI (FIG. 3) was amplified in all *S. lugdunensis* isolates except IDRL-2492 and IDRL-2639. A 4.9 kb product that encompasses the ORF-icaADBC region (FIG. 3) was amplified from the two remaining isolates, indicating that the ORF-icaADBC genes are intact in all isolates in our collection.

The following was performed to determine whether the variability in biofilm formation among *S. lugdunensis* isolates (FIG. 1D) could be explained by differences in the ORF-icaADBC primary sequence. In addition to the two isolates that were sequenced by restriction-site PCR (IDRL-2414 and IDRL-2664), 7.6 kb PCR products from IDRL-5204, IDRL-5256, and IDRL-5258 were sequenced. These isolates included a poor biofilm producer (IDRL-5204), intermediate biofilm producers (IDRL-2414, IDRL-2664), and strong biofilm producers (IDRL-5256, IDRL-5258) (FIG. 1D). The sequences of IDRL-2414, IDRL-2664, and IDRL-5204 were identical, but the sequences of the strongest biofilm formers were different at one or more locations. IDRL-5258 contained an R274Q change at amino acid 274 of IcaA. IDRL-5256 contained many single nucleotide changes throughout the sequenced region. Eleven variations were found in the yycJ-ORF intergenic region; one variation occurred in the ORF-icaA intergenic region; and four variations were located between icaC-yycI. In addition, the following silent (non-coding) and coding mutations were found in each of the coding regions: yycJ-6 silent; ORF-4 silent, S26A, E44D; icaA: 8 silent; icaD: 4 silent; icaB: 4 silent, H23Q; icaC: 3 silent; yycI-4 silent. Despite the correlation of sequence variations found in the most proficient biofilm forming isolates, it is not clear from these results whether the ORF-icaADBC locus primary sequence is a contributing factor in the relative ability of *S. lugdunensis* isolates to form biofilm.

Elucidation of the Role of PNAG in *S. lugdunensis* Biofilm Formation

Figure 4:
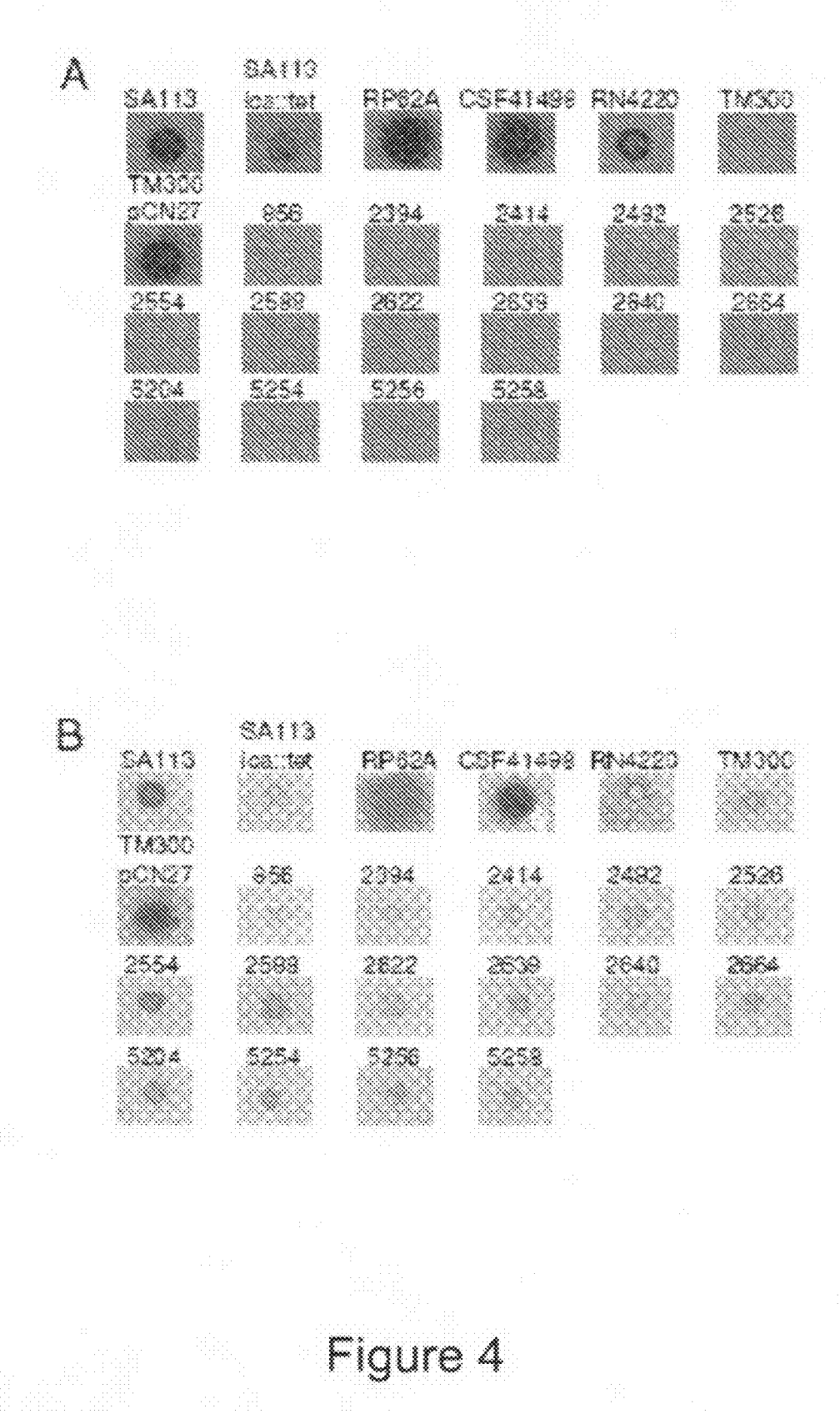

The functional role of the *S. lugdunensis* icaADBC genes in biofilm formation was tested by assaying for PNAG in static phase or biofilm cells. Extracts from static phase cells were blotted on nitrocellulose membranes and probed with labeled wheat germ agglutinin (WGA). PNAG was strongly detected in *S. epidermidis* strains RP62A and CSF41498, and a PNAG over-expressing strain of *S. carnosus* TM300 that carries plasmid pCN27 (FIG. 4A). PNAG production by *S. aureus* strains RN4220 and SA113 was less abundant. A minimal signal was apparent in the PNAG-negative SA113 ica::tet isogenic knockout strain, most likely due to non-biofilm sources of N-acetylglucosamine. Unexpectedly, PNAG was not detected in any of the 15 *S. lugdunensis* isolate. PNAG was also not detected in the negative control strain *S. carnosus* TM300.

To confirm the lack of detection of PNAG from *S. lugdunensis* cells, immunoblotting experiments with static phase cells (data not shown) and biofilm cells (FIG. 4B) were performed using an anti-deacetylated PNAG antibody. Signal levels from all *S. lugdunensis* strains were equivalent to the non-PNAG producing *S. aureus* SA113 ica::tet and *S. carnosus* TM300 negative controls.

Figure 6:
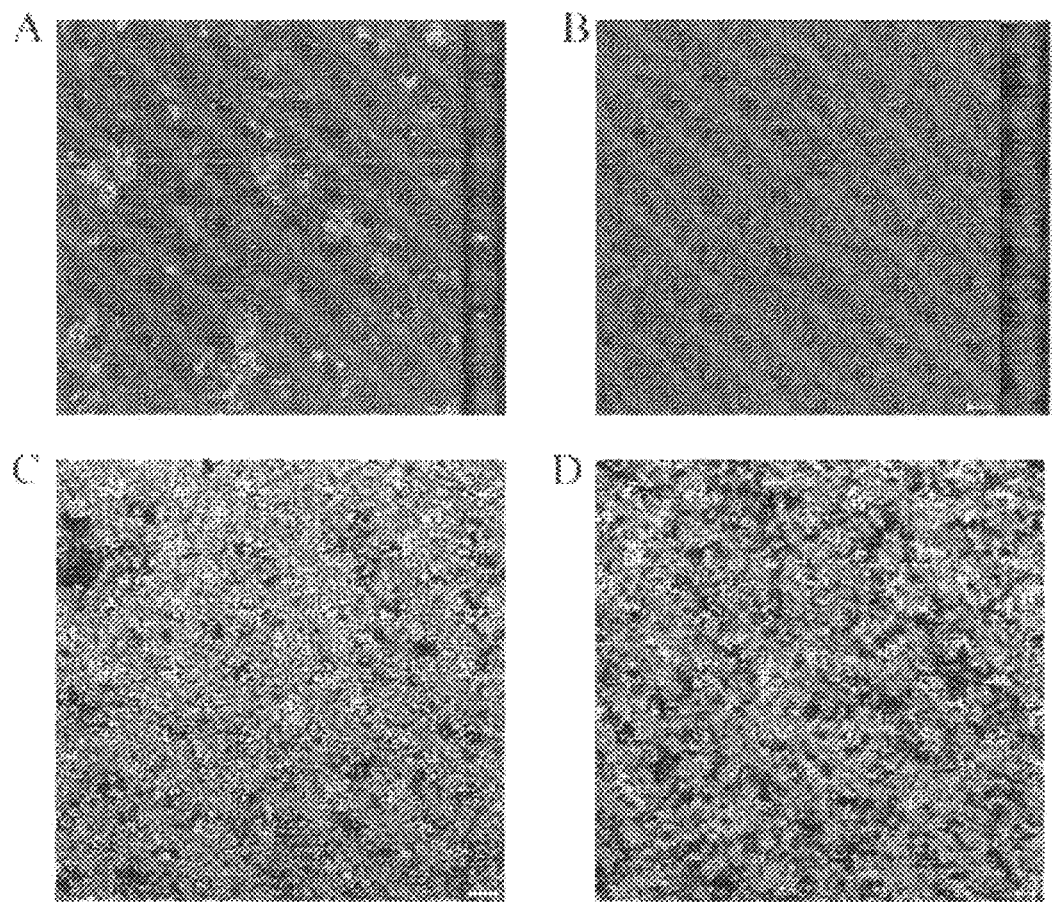
FIG. 6. Assessment of the *S. lugdunensis* biofilm extracellular matrix with confocal scanning laser microscopy. Biofilms were grown in chambered coverglass wells, stained, and visualized by CSLM with a 100× oil immersion objection. A, B. Microscopic visualization of the presence or absence of PNAG in the biofilm extracellular matrix of *S. epidermidis* RP62A (A) or *S. lugdunensis* IDRL-2640 (B). Large PNAG structures (green), stained with fluorescently labeled wheat germ agglutinin, were located among cells (red), stained with the lipophilic membrane dye FM 4-64, in *S. epidermidis* RP62A biofilms but not *S. lugdunensis* IDRL-2640 biofilms. Images show a single X-Y slice from the center of the biofilm and the biofilm profile from the Y-Z axis (right). C, D. Detection of extracellular proteins in biofilms of *S. epidermidis* RP62A (C) and *S. lugdunensis* IDRL-5258 (D). Polypeptides (red) were stained with SYPRO Ruby. Bacteria were stained with Syto-9, a vital nucleic acid stain. Yellow areas indicate polypeptide and cellular co-localization. Bar=5 μm.

CSLM was used to visualize *S. lugdunensis* biofilms in comparison with biofilms formed by PNAG-producing *S. epidermidis* RP62A (FIG. 6A,B). Cells were stained with FM 4-64, a red lipophilic plasma membrane dye, and PNAG was stained with Oregon green conjugated wheat germ agglutinin. *S. epidermidis* RP62A formed a thick, multi-layered biofilm interspersed with large and abundant structures of PNAG (FIG. 6A). In contrast, under identical microscopy settings, *S. lugdunensis* IDRL-2640 formed a thick and dense biofilm void of detectable PNAG (FIG. 6B). Similar results were observed with *S. lugdunensis* IDRL-5258 biofilms. These images indicate that (1) *S. lugdunensis* isolates are able to form thick, multi-cellular biofilms, and (2) PNAG is not a recognizable component of *S. lugdunensis* in vitro biofilms.

Screen for Other Extracellular Matrix Polysaccharides

In the absence of PNAG, alternative polysaccharides may be present in the matrix of *S. lugdunensis* biofilms. Six lectins—concanavalin A (binds glucose and mannose), DBA (binds N-acetylgalactosamine), SBA (binds galactose and N-acetylgalactosamine), PNA (binds galactose), $RCA_{120}$ (binds galactose and N-acetylgalactosamine), and UEA-1 (binds fucose)—were chosen to assay for other extracellular matrix polysaccharides in *S. lugdunensis* static phase cell extracts by immunoblotting. Concanavalin A bound to all staphylococcal strains tested, which was not unexpected based on its broad specificity for common sugars. SBA selectively bound to *S. carnosus* isolates, and $RCA_{120}$ selectively bound to *S. epidermidis* and the *S. carnosus* PNAG overexpressing strain. However, none of the lectins bound to the *S. lugdunensis* extracts, providing evidence that several other types of polysaccharides, in addition to PNAG, are not part of the *S. lugdunensis* biofilm matrix.

Figure 5A:
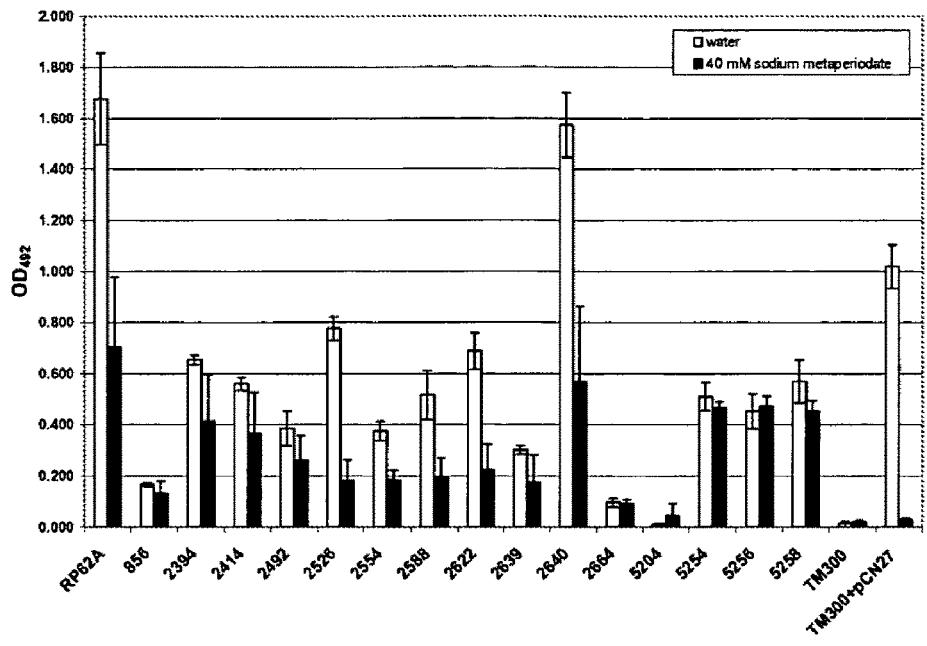
FIG. 5. *S. lugdunensis* biofilms are susceptible to detachment by proteases but not carbohydrate-degrading reagents. 24 hours biofilms of *S. epidermidis* RP62A, *S. carnosus* TM300, *S. carnosus* TM300+pCN27, and *S. lugdunensis* clinical isolates formed in microtiter plates were washed and incubated with various chemical or enzymatic treatments for 2 hours at 37° C. to determine which agents could detach *S. lugdunensis* biofilms. Biofilm remaining in wells after treatment was stained with 0.1% safranin, resuspended in 30% glacial acetic acid, and quantitated on a plate reader at OD492 nm. A. Sodium metaperiodate treatment. B. Dispersin B treatment. C. Proteinase K treatment. D. Trypsin treatment. Bars are the average of stained biofilm remaining in four wells after treatment. Error bars show the standard deviation. Asterisks indicate statistically significant decreases in biofilm detachment after treatment compared to biofilm detachment in the corresponding buffer (P-value<0.05, Student's t-test). Data are representative of two or three replicate experiments with similar results.
Figure 5B:
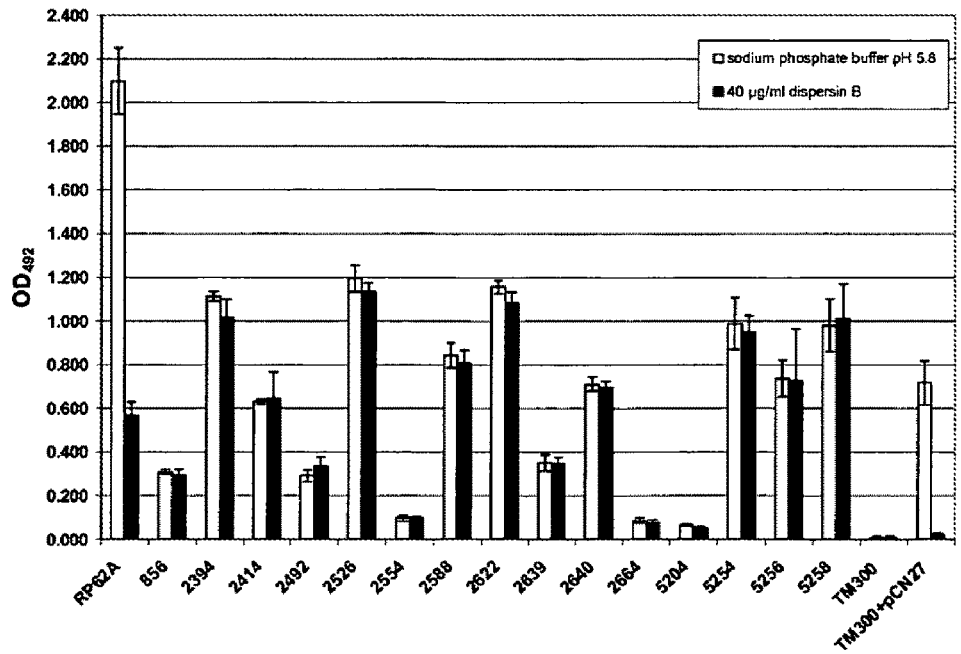

Detachment of *S. lugdunensis* Biofilms with Proteases but not Carbohydrate-Degrading Reagents A chemical and enzymatic detachment approach was used to examine the composition of the biofilm matrix. Sodium metaperiodate and dispersin B degrade PNAG, thereby releasing PNAG-containing biofilms from their associated surfaces (Kaplan et al., *J. Bacteriol.*, 185:4693-8 (2003); Kaplan et al., *Antimicrob. Agents Chemother.*, 48:2633-2636 (2004); and Wang et al., *J. Bacteriol.*, 186:2724-2734 (2004)). As expected, pre-formed biofilms of *S. epidermidis* RP62A and PNAG over-producing *S. carnosus* TM300+ pCN27 that were treated with sodium metaperiodate (FIG. 5A) and dispersin B (FIG. 5B) were susceptible to detachment by both reagents (P-value≦0.001, Student's t-test). *S. carnosus* biofilms, which likely contain high amounts of PNAG without additional stabilizing factors, were essentially completely released from microtiter wells, compared to buffer-only treatment controls. In contrast, despite substantial detachment, much greater levels of *S. epidermidis* RP62A biofilms remained after treatment with either sodium metaperiodate or dispersin B. The biofilm matrix components of this strain are known to include extracellular teichoic acids and polypeptides, in addition to large amounts of PNAG, which may have assisted in protecting or stabilizing the biofilm from detachment. Confirmatory of the immunoblotting and microscopy data, *S. lugdunensis* biofilms resisted detachment by dispersin B (FIG. 5B). *S. lugdunensis* IDRL-2622 was the only isolate that exhibited statistically significant, yet minimal, detachment following incubation with dispersin B (P-value=0.045, Student's t-test). In addition, sodium metaperiodate had moderate to little effect on the release of 53% (8/15) *S. lugdunensis* biofilms (FIG. 5A). Seven *S. lugdunen-* sis biofilms (IDRL-2394, IDRL-2526, IDRL-2554, IDRL-2588, IDRL-2622, IDRL-2640, and IDRL-5258) demonstrated greater susceptibility to sodium metaperiodate (P-value≦0.047, Student's t-test), suggesting that the biochemical constituents in the extracellular matrix of S. lugdunensis biofilms may vary among isolates.

Figure 5C:
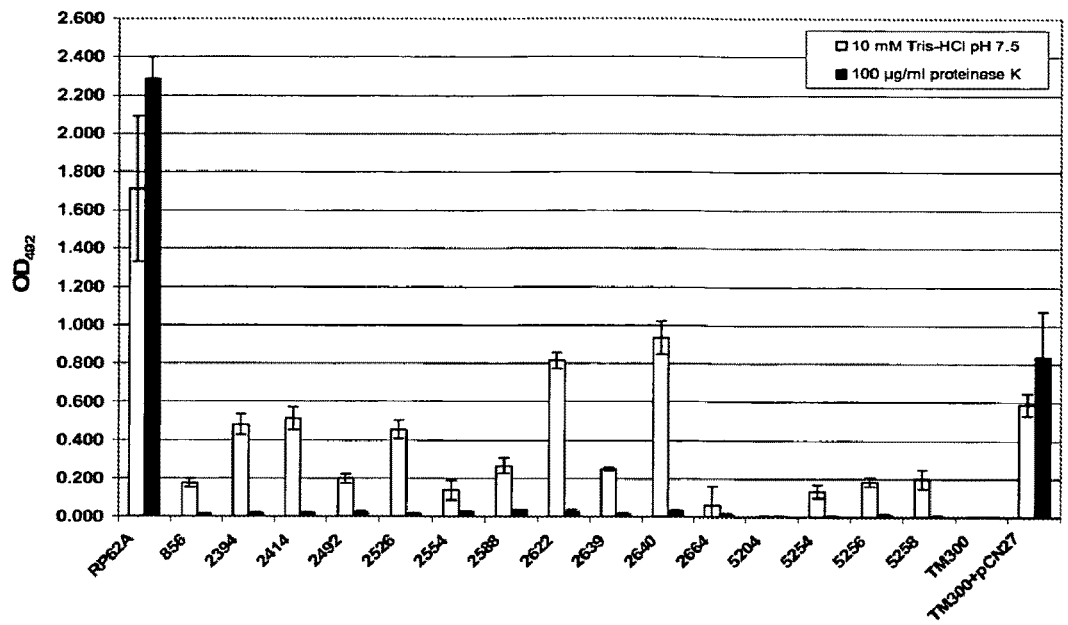
Figure 5D:
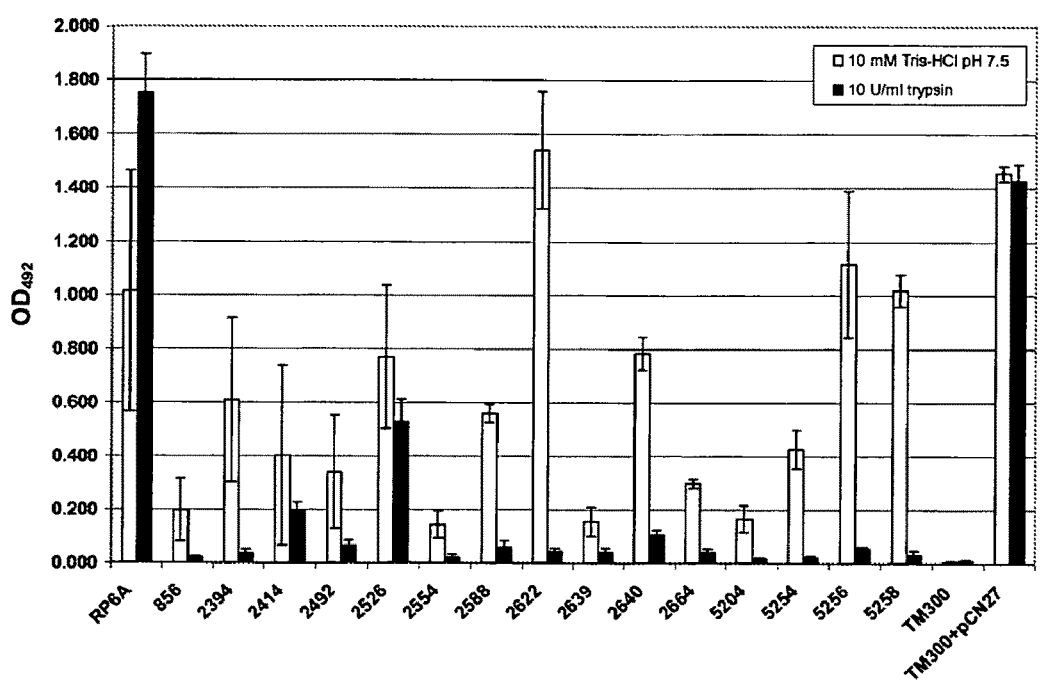

The ability of several proteases with varying substrate specificities to detach biofilms of S. lugdunensis and the PNAG-containing control strains was tested. Proteinase K had no effect on the PNAG-positive control strains, while biofilm of all S. lugdunensis isolates that formed substantial biofilms were completely removed (FIG. 5C; P-value≦0.005, Student's t-test). In order to demonstrate that the overwhelming detachment of S. lugdunensis biofilms was due to the enzymatic activity of proteinase K, the experiment was repeated with heat-inactivated proteinase K, and the detachment effect was found to be abolished upon proteinase K denaturation. Concordant results were obtained upon treatment of biofilms with trypsin (FIG. 5D, P-value≦0.041, Student's t-test), except that a few S. lugdunensis isolates (IDRL-2414 and IDRL-2526) were noticeably more resistant to release by trypsin. Two other proteases, thermolysin and chymotrypsin, were also found to detach S. lugdunensis biofilms selectively, but not PNAG-containing biofilms formed by S. epidermidis RP62A or S. carnosus TM300+pCN27. These results provide evidence that polypeptides are important for S. lugdunensis in vitro biofilm formation on polystyrene when cells are grown in $TSB_{gluc1\%}$.

Visualization of Extracellular Proteins in S. lugdunensis Biofilms by CSLM

Biofilms of S. epidermidis RP62A and S. lugdunensis IDRL-5258 were stained with the red fluorescent protein dye SYPRO Ruby in order to visualize extracellular polypeptides among biofilm cells, which were stained with the green nucleic acid stain Syto-9. Extracellular polypeptides were visible in biofilms of both S. epidermidis RP62A (FIG. 6C) and S. lugdunensis IDRL-5258 (FIG. 6D). S. lugdunensis biofilms appeared to contain more polypeptides than S. epidermidis biofilms. To more accurately assess the relative abundance of extracellular polypeptides per number of cells in biofilms formed by either organism, the ratio of polypeptide to cell fluorescence was calculated. The average polypeptide to cell fluorescence measured in S. lugdunensis IDRL-5258 biofilms was statistically higher than the same measurement in S. epidermidis RP62A biofilms (0.965, 0.285SD versus 0.385, 0.114SD, respectively; P-value<0.01, Student's t-test), supporting the hypothesis that polypeptides are a significant component of this organism's biofilm matrix.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated and substantially pure polypeptide having glycosyl hydrolase activity and comprising an amino acid sequence having a length of at least 300 amino acid residues and at least about 95 percent identity to the amino acid sequence set forth in SEQ ID NO:2 over said length.

2. The polypeptide of claim 1, wherein said amino acid sequence comprises at least about 99 percent identity to the amino acid sequence set forth in SEQ ID NO:2 over said length.

3. The polypeptide of claim 1, wherein said polypeptide is encoded by a nucleic acid molecule comprising the nucleic acid sequence set forth in SEQ ID NO:1.

4. The polypeptide of claim 1, wherein said polypeptide comprises the amino acid sequence set forth in SEQ ID NO:2.

* * * * *

SEQUENCE LISTING

```
<160> NUMBER OF SEQ ID NOS: 89

<210> SEQ ID NO 1
<211> LENGTH: 1035
<212> TYPE: DNA
<213> ORGANISM: Staphylococcus lugdunensis

<400> SEQUENCE: 1
atgaaaaagc ttagtgccat tattgttatt ttattactta ttgtattcac tttctttcct      60
aagcatagta agcaatctga tattgaaaag ggtatttcta ttgatattgc acggacgcat     120
tatactaaag agagtattaa gaaaatcatc ggcgagctta gccgtgtcaa tgggcgttat     180
ctacaattac accttgctga caatgacaat tatagtattt actcaaatgt cttaggtcaa     240
acgtctaccc attcaaatca ctattacctc acaaaagcag aattgcgtga gcttgttcaa     300
tatgccaata aacaccatgt ccagcttatt cctgaattag acttccctgc acattcaaaa     360
gccatgctga cgttactcca taaacatcat ccctctcaat atcgacaggt tgtttctagc     420
tatgataata caatgcttga ttttcaacaa atcagacag cgcttgatgt atctcgtcag     480
ttaatcaatg aagttgctga tattttctat caaacaccgt ataagacaa tttaaaaatg     540 gttatcggtg gagatgaggt acctggtgga ggcgcacagc aacgtgattt tgtttcatac     600
atgaatcagc ttgcagacac tgtccaagca aagcattata cgcctaagat gtggaatgat     660
tctttgacac atgaaggact caaaaattta aatcacagca ttattattat gtattggcat     720
caaccatcca aacagtcacc atcgccaact gactttttca ctaaccactt tatggtcgaa     780
aattttaatc gttctgttta ctacgtcttt cctagagcac agcaaagcac acattcgtta     840
gctaagcaga aagctgatat tgccgacaca cgtttaacag attttaatac agctaatatg     900
cgtaaagacc cgcatttcaa tagttatatt aatggtgaat atctcacatt ttggggagaa     960
```

```
tttgcttcag atttaaaaca gaccaattta atcgagtatg tatataagtt tattcgcatt   1020
tattttaatt cctaa                                                    1035
```

<210> SEQ ID NO 2
<211> LENGTH: 344
<212> TYPE: PRT
<213> ORGANISM: Staphylococcus lugdunensis

<400> SEQUENCE: 2

```
Met Lys Lys Leu Ser Ala Ile Ile Val Ile Leu Leu Ile Val Phe
 1               5                  10                  15

Thr Phe Phe Pro Lys His Ser Lys Gln Ser Asp Ile Glu Lys Gly Ile
                20                  25                  30

Ser Ile Asp Ile Ala Arg Thr His Tyr Thr Lys Glu Ser Ile Lys Lys
            35                  40                  45

Ile Ile Gly Glu Leu Ser Arg Val Asn Gly Arg Tyr Leu Gln Leu His
        50                  55                  60

Leu Ala Asp Asn Asp Asn Tyr Ser Ile Tyr Ser Asn Val Leu Gly Gln
65                  70                  75                  80

Thr Ser Thr His Ser Asn His Tyr Tyr Leu Thr Lys Ala Glu Leu Arg
                85                  90                  95

Glu Leu Val Gln Tyr Ala Asn Lys His His Val Gln Leu Ile Pro Glu
            100                 105                 110

Leu Asp Phe Pro Ala His Ser Lys Ala Met Leu Thr Leu Leu His Lys
        115                 120                 125

His His Pro Ser Gln Tyr Arg Gln Val Val Ser Ser Tyr Asp Asn Thr
    130                 135                 140

Met Leu Asp Phe Gln Gln Asn Gly Thr Ala Leu Asp Val Ser Arg Gln
145                 150                 155                 160

Leu Ile Asn Glu Val Ala Asp Ile Phe Tyr Gln Thr Pro Tyr Lys Asp
                165                 170                 175

Asn Leu Lys Met Val Ile Gly Gly Asp Glu Val Pro Gly Gly Gly Ala
            180                 185                 190

Gln Gln Arg Asp Phe Val Ser Tyr Met Asn Gln Leu Ala Asp Thr Val
        195                 200                 205

Gln Ala Lys His Tyr Thr Pro Lys Met Trp Asn Asp Ser Leu Thr His
    210                 215                 220

Glu Gly Leu Lys Asn Leu Asn His Ser Ile Ile Met Tyr Trp His
225                 230                 235                 240

Gln Pro Ser Lys Gln Ser Pro Ser Pro Thr Asp Phe Phe Thr Asn His
                245                 250                 255

Phe Met Val Glu Asn Phe Asn Arg Ser Val Tyr Tyr Val Phe Pro Arg
            260                 265                 270

Ala Gln Gln Ser Thr His Ser Leu Ala Lys Gln Lys Ala Asp Ile Ala
        275                 280                 285

Asp Thr Arg Leu Thr Asp Phe Asn Thr Ala Asn Met Arg Lys Asp Pro
    290                 295                 300

His Phe Asn Ser Tyr Ile Asn Gly Glu Tyr Leu Thr Phe Trp Gly Glu
305                 310                 315                 320

Phe Ala Ser Asp Leu Lys Gln Thr Asn Leu Ile Glu Tyr Val Tyr Lys
                325                 330                 335

Phe Ile Arg Ile Tyr Phe Asn Ser
            340
```

```
<210> SEQ ID NO 3
<211> LENGTH: 377
<212> TYPE: PRT
<213> ORGANISM: Actinobacillus pleuropneumoniae

<400> SEQUENCE: 3

Met Lys Lys Ala Ile Thr Leu Phe Thr Leu Leu Cys Ala Val Leu Leu
 1               5                  10                  15

Ser Phe Ser Thr Ala Thr Tyr Ala Asn Ala Met Asp Leu Pro Lys Lys
            20                  25                  30

Glu Ser Gly Leu Thr Leu Asp Ile Ala Arg Arg Phe Tyr Thr Val Asp
        35                  40                  45

Thr Ile Lys Gln Phe Ile Asp Thr Ile His Gln Ala Gly Gly Thr Phe
 50                  55                  60

Leu His Leu His Phe Ser Asp His Glu Asn Tyr Ala Leu Glu Ser Ser
 65                  70                  75                  80

Tyr Leu Glu Gln Arg Glu Glu Asn Ala Thr Glu Lys Asn Gly Thr Tyr
                85                  90                  95

Phe Asn Pro Lys Thr Asn Lys Pro Phe Leu Thr Tyr Lys Gln Leu Asn
            100                 105                 110

Glu Ile Ile Tyr Tyr Ala Lys Glu Arg Asn Ile Glu Ile Val Pro Glu
        115                 120                 125

Val Asp Ser Pro Asn His Met Thr Ala Ile Phe Asp Leu Leu Thr Leu
130                 135                 140

Lys His Gly Lys Glu Tyr Val Lys Gly Leu Lys Ser Pro Tyr Ile Ala
145                 150                 155                 160

Glu Glu Ile Asp Ile Asn Asn Pro Glu Ala Val Glu Val Ile Lys Thr
                165                 170                 175

Leu Ile Gly Glu Val Ile Tyr Ile Phe Gly His Ser Ser Arg His Phe
            180                 185                 190

His Ile Gly Gly Asp Glu Phe Ser Tyr Ala Val Glu Asn Asn His Glu
        195                 200                 205

Phe Ile Arg Tyr Val Asn Thr Leu Asn Asp Phe Ile Asn Ser Lys Gly
210                 215                 220

Leu Ile Thr Arg Val Trp Asn Asp Gly Leu Ile Lys Asn Asn Leu Ser
225                 230                 235                 240

Glu Leu Asn Lys Asn Ile Glu Ile Thr Tyr Trp Ser Tyr Asp Gly Asp
                245                 250                 255

Ala Gln Ala Lys Glu Asp Ile Gln Tyr Arg Arg Glu Ile Arg Ala Asp
            260                 265                 270

Leu Pro Glu Leu Leu Ala Asn Gly Phe Lys Val Leu Asn Tyr Asn Ser
        275                 280                 285

Tyr Tyr Leu Tyr Phe Val Pro Lys Ser Gly Ser Asn Ile His Asn Asp
290                 295                 300

Gly Lys Tyr Ala Ala Glu Asp Val Leu Asn Asn Trp Thr Leu Gly Lys
305                 310                 315                 320

Trp Asp Gly Lys Asn Ser Ser Asn His Val Gln Asn Thr Gln Asn Ile
                325                 330                 335

Ile Gly Ser Ser Leu Ser Ile Trp Gly Glu Arg Ser Ser Ala Leu Asn
            340                 345                 350

Glu Gln Thr Ile Gln Gln Ala Ser Lys Asn Leu Leu Lys Ala Val Ile
        355                 360                 365

Gln Lys Thr Asn Asp Pro Lys Ser His
        370                 375
```

```
<210> SEQ ID NO 4
<211> LENGTH: 361
<212> TYPE: PRT
<213> ORGANISM: Actinobacillus actinomycetemcomitans

<400> SEQUENCE: 4

Asn Cys Cys Val Lys Gly Asn Ser Ile Tyr Pro Gln Lys Thr Ser Thr
 1               5                  10                  15

Lys Gln Thr Gly Leu Met Leu Asp Ile Ala Arg His Phe Tyr Ser Pro
            20                  25                  30

Glu Val Ile Lys Ser Phe Ile Asp Thr Ile Ser Leu Ser Gly Gly Asn
        35                  40                  45

Phe Leu His Leu His Phe Ser Asp His Glu Asn Tyr Ala Ile Glu Ser
50                  55                  60

His Leu Leu Asn Gln Arg Ala Glu Asn Ala Val Gln Gly Lys Asp Gly
65                  70                  75                  80

Ile Tyr Ile Asn Pro Tyr Thr Gly Lys Pro Phe Leu Ser Tyr Arg Gln
                85                  90                  95

Leu Asp Asp Ile Lys Ala Tyr Ala Lys Ala Lys Gly Ile Glu Leu Ile
            100                 105                 110

Pro Glu Leu Asp Ser Pro Asn His Met Thr Ala Ile Phe Lys Leu Val
        115                 120                 125

Gln Lys Asp Arg Gly Val Lys Tyr Leu Gln Gly Leu Lys Ser Arg Gln
130                 135                 140

Val Asp Asp Glu Ile Asp Ile Thr Asn Ala Asp Ser Ile Thr Phe Met
145                 150                 155                 160

Gln Ser Leu Met Ser Glu Val Ile Asp Ile Phe Gly Asp Thr Ser Gln
                165                 170                 175

His Phe His Ile Gly Gly Asp Glu Phe Gly Tyr Ser Val Glu Ser Asn
            180                 185                 190

His Glu Phe Ile Thr Tyr Ala Asn Lys Leu Ser Tyr Phe Leu Glu Lys
        195                 200                 205

Lys Gly Leu Lys Thr Arg Met Trp Asn Asp Gly Leu Ile Lys Asn Thr
210                 215                 220

Phe Glu Gln Ile Asn Pro Asn Ile Glu Ile Thr Tyr Trp Ser Tyr Asp
225                 230                 235                 240

Gly Asp Thr Gln Asp Lys Asn Glu Ala Ala Glu Arg Arg Asp Met Arg
                245                 250                 255

Val Ser Leu Pro Glu Leu Leu Ala Lys Gly Phe Thr Val Leu Asn Tyr
            260                 265                 270

Asn Ser Tyr Tyr Leu Tyr Ile Val Pro Lys Ala Ser Pro Thr Phe Ser
        275                 280                 285

Gln Asp Ala Ala Phe Ala Ala Lys Asp Val Ile Lys Asn Trp Asp Leu
290                 295                 300

Gly Val Trp Asp Gly Arg Asn Thr Lys Asn Arg Val Gln Asn Thr His
305                 310                 315                 320

Glu Ile Ala Gly Ala Ala Leu Ser Ile Trp Gly Glu Asp Ala Lys Ala
                325                 330                 335

Leu Lys Asp Glu Thr Ile Gln Lys Asn Thr Lys Ser Leu Leu Glu Ala
            340                 345                 350

Val Ile His Lys Thr Asn Gly Asp Glu
        355                 360

<210> SEQ ID NO 5
<211> LENGTH: 1035
<212> TYPE: DNA
```

-continued

```
<213> ORGANISM: Staphylococcus lugdunensis

<400> SEQUENCE: 5
atgaaaaagc ttagtgccat tattgttatt ttattactta ttgtattcac tttctttcct      60
aagcatagta agcaagctga tattgaaaag ggtatttcta ttgatattgc acggacgcat     120
tatactaaag atagcattaa gaaaatcatc ggcgagctta gccgtgtcaa tgggcgttat     180
ctacaattac accttgctga caatgacaat tatagtattt actcaaatgt cttaggtcaa     240
acgtctaccc attcaaatca ctattacctc acaaaagcag aattgcgtga gcttgttcaa     300
tatgccaata acaccatgt ccagcttatt cctgaattag acttccctgc acattcaaaa     360
gccatgctga cgttactcca taaacatcat ccctctcaat atcgacaggt tgtttctagc     420
tatgataata caatgcttga ttttcaacaa aatcagacag cgcttgatgt atctcgtcag     480
ttaatcaatg aagttgctga tattttctat caaacaccgt ataaagacaa tttaaaaatg     540
gttatcggtg gagatgaggt acctggtgga ggcgcacagc aacgtgattt tgtttcatac     600
atgaatcagc ttgcagacac tgtccaagca aagcattata cgcctaagat gtggaatgac     660
tctttgacac atgaaggact caaaaattta aatcacagca ttattattat gtattggcat     720
caaccatcca aacagtcacc atcgccaact gacttttca ctaaccactt tatggtcgaa     780
aattttaatc gttctgttta ctatgtcttt cctagagcac agcaaagcac acattcgtta     840
gctaagcaga aagctgatat tgccgacaca cgtttaacag attttaatac agctaatatg     900
cgtaaagatc cgcatttcaa tagttatatt aatggtgaat atctcacatt ttggggagaa     960
tttgcttcag atttaaaaca gaccaattta atcgagtatg tatataagtt tattcgcatt    1020
tattttaatt cctaa                                                     1035

<210> SEQ ID NO 6
<211> LENGTH: 344
<212> TYPE: PRT
<213> ORGANISM: Staphylococcus lugdunensis

<400> SEQUENCE: 6

Met Lys Lys Leu Ser Ala Ile Ile Val Ile Leu Leu Ile Val Phe
 1               5                  10                  15

Thr Phe Pro Lys His Ser Lys Gln Ala Asp Ile Glu Lys Gly Ile
                20                  25                  30

Ser Ile Asp Ile Ala Arg Thr His Tyr Thr Lys Asp Ser Ile Lys Lys
            35                  40                  45

Ile Ile Gly Glu Leu Ser Arg Val Asn Gly Arg Tyr Leu Gln Leu His
        50                  55                  60

Leu Ala Asp Asn Asp Asn Tyr Ser Ile Tyr Ser Asn Val Leu Gly Gln
65                  70                  75                  80

Thr Ser Thr His Ser Asn His Tyr Tyr Leu Thr Lys Ala Glu Leu Arg
                85                  90                  95

Glu Leu Val Gln Tyr Ala Asn Lys His His Val Gln Leu Ile Pro Glu
            100                 105                 110

Leu Asp Phe Pro Ala His Ser Lys Ala Met Leu Thr Leu Leu His Lys
        115                 120                 125

His His Pro Ser Gln Tyr Arg Gln Val Val Ser Ser Tyr Asp Asn Thr
    130                 135                 140

Met Leu Asp Phe Gln Gln Asn Gln Thr Ala Leu Asp Val Ser Arg Gln
145                 150                 155                 160

Leu Ile Asn Glu Val Ala Asp Ile Phe Tyr Gln Thr Pro Tyr Lys Asp
                165                 170                 175
```

```
Asn Leu Lys Met Val Ile Gly Gly Asp Glu Val Pro Gly Gly Gly Ala
        180                 185                 190

Gln Gln Arg Asp Phe Val Ser Tyr Met Asn Gln Leu Ala Asp Thr Val
    195                 200                 205

Gln Ala Lys His Tyr Thr Pro Lys Met Trp Asn Asp Ser Leu Thr His
    210                 215                 220

Glu Gly Leu Lys Asn Leu Asn His Ser Ile Ile Met Tyr Trp His
225                 230                 235                 240

Gln Pro Ser Lys Gln Ser Pro Ser Pro Thr Asp Phe Thr Asn His
            245                 250                 255

Phe Met Val Glu Asn Phe Asn Arg Ser Val Tyr Tyr Val Phe Pro Arg
        260                 265                 270

Ala Gln Gln Ser Thr His Ser Leu Ala Lys Gln Lys Ala Asp Ile Ala
    275                 280                 285

Asp Thr Arg Leu Thr Asp Phe Asn Thr Ala Asn Met Arg Lys Asp Pro
290                 295                 300

His Phe Asn Ser Tyr Ile Asn Gly Glu Tyr Leu Thr Phe Trp Gly Glu
305                 310                 315                 320

Phe Ala Ser Asp Leu Lys Gln Thr Asn Leu Ile Glu Tyr Val Tyr Lys
            325                 330                 335

Phe Ile Arg Ile Tyr Phe Asn Ser
            340

<210> SEQ ID NO 7
<211> LENGTH: 19
<212> TYPE: DNA
<213> ORGANISM: Artificial Sequence
<220> FEATURE:
<223> OTHER INFORMATION: Synthetically generated oligonucleotide

<400> SEQUENCE: 7
cctctgtctg ggcttgacc                                                19

<210> SEQ ID NO 8
<211> LENGTH: 20
<212> TYPE: DNA
<213> ORGANISM: Artificial Sequence
<220> FEATURE:
<223> OTHER INFORMATION: Synthetically generated oligonucleotide

<400> SEQUENCE: 8
gatggaagtt ctgataatac                                               20

<210> SEQ ID NO 9
<211> LENGTH: 25
<212> TYPE: DNA
<213> ORGANISM: Artificial Sequence
<220> FEATURE:
<223> OTHER INFORMATION: Synthetically generated oligonucleotide

<400> SEQUENCE: 9
gtgaaaacac ctgaaatagt attga                                         25

<210> SEQ ID NO 10
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 10
```
ttgaaggata agattattga taac                                    24

<210> SEQ ID NO 11
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 11
tagtagcgaa tacacttcat c                                       21

<210> SEQ ID NO 12
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 12
ttgaaagata agattattga taac                                    24

<210> SEQ ID NO 13
<211> LENGTH: 22
<212> TYPE: DNA
<213> ORGANISM: Artificial Sequence
<220> FEATURE:
<223> OTHER INFORMATION: Synthetically generated oligonucleotide

<400> SEQUENCE: 13
catttaacag tgaatatact tg                                      22

<210> SEQ ID NO 14
<211> LENGTH: 39
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 24, 25, 26, 27, 28, 29, 30, 31, 32, 33
<223> OTHER INFORMATION: n = A, T, C, or G

<400> SEQUENCE: 14
ggtacctaat acgactcact atannnnnnn nnnggatcc                    39

<210> SEQ ID NO 15
<211> LENGTH: 39
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 24, 25, 26, 27, 28, 29, 30, 31, 32, 33
<223> OTHER INFORMATION: n = A,T,C or G

<400> SEQUENCE: 15
ggtacctaat acgactcact atannnnnnn nnngaattc                    39

<210> SEQ ID NO 16
<211> LENGTH: 37
<212> TYPE: DNA
<213> ORGANISM: Artificial Sequence
<220> FEATURE:
<223> OTHER INFORMATION: Synthetically generated oligonucleotide
<220> FEATURE:
<220> FEATURE:
<221> NAME/KEY: misc_feature

```
<222> LOCATION: 24, 25, 26, 27, 28, 29, 30, 31, 32, 33
<223> OTHER INFORMATION: n = A,T,C or G

<400> SEQUENCE: 16
ggtacctaat acgactcact atannnnnnn nnngatc                              37

<210> SEQ ID NO 17
<211> LENGTH: 37
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 24, 25, 26, 27, 28, 29, 30, 31, 32, 33
<223> OTHER INFORMATION: n = A,T,C or G

<400> SEQUENCE: 17
ggtacctaat acgactcact atannnnnnn nnntcga                              37

<210> SEQ ID NO 18
<211> LENGTH: 20
<212> TYPE: DNA
<213> ORGANISM: Artificial Sequence
<220> FEATURE:
<223> OTHER INFORMATION: Synthetically generated oligonucleotide

<400> SEQUENCE: 18
caaaaaaacc aagggtaaag                                                 20

<210> SEQ ID NO 19
<211> LENGTH: 23
<212> TYPE: DNA
<213> ORGANISM: Artificial Sequence
<220> FEATURE:
<223> OTHER INFORMATION: Synthetically generated oligonucleotide

<400> SEQUENCE: 19
acctaaaata gacttcttat ttc                                             23

<210> SEQ ID NO 20
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 20
cccatcacta gatcatattg t                                               21

<210> SEQ ID NO 21
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 21
atgttagaac attttatcga t                                               21

<210> SEQ ID NO 22
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 22
```
atcgataaaa tgttctaaca t                                              21

<210> SEQ ID NO 23
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 23
aatccgaaat tggctgcggt a                                              21

<210> SEQ ID NO 24
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 24
tttaacgagg aagagacgat t                                              21

<210> SEQ ID NO 25
<211> LENGTH: 20
<212> TYPE: DNA
<213> ORGANISM: Artificial Sequence
<220> FEATURE:
<223> OTHER INFORMATION: Synthetically generated oligonucleotide

<400> SEQUENCE: 25
gaatcagaac ttcttgccca                                                20

<210> SEQ ID NO 26
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 26
tatttggaaa ctctaacgat a                                              21

<210> SEQ ID NO 27
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 27
agccacgcgc attatgtcga a                                              21

<210> SEQ ID NO 28
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 28
tgcttgttcc tgagacgata c                                              21

<210> SEQ ID NO 29
<211> LENGTH: 22
<212> TYPE: DNA
<213> ORGANISM: Artificial Sequence

```
<220> FEATURE:
<223> OTHER INFORMATION: Synthetically generated oligonucleotide

<400> SEQUENCE: 29
tcgtctcttc ctcgttaaaa ca                                              22

<210> SEQ ID NO 30
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 30
attaaaaagg aaatacct                                                   18

<210> SEQ ID NO 31
<211> LENGTH: 22
<212> TYPE: DNA
<213> ORGANISM: Artificial Sequence
<220> FEATURE:
<223> OTHER INFORMATION: Synthetically generated oligonucleotide

<400> SEQUENCE: 31
aacgtcttcg atgggcacaa gg                                              22

<210> SEQ ID NO 32
<211> LENGTH: 23
<212> TYPE: DNA
<213> ORGANISM: Artificial Sequence
<220> FEATURE:
<223> OTHER INFORMATION: Synthetically generated oligonucleotide

<400> SEQUENCE: 32
cagcaaagca cacattcgtt agc                                             23

<210> SEQ ID NO 33
<211> LENGTH: 22
<212> TYPE: DNA
<213> ORGANISM: Artificial Sequence
<220> FEATURE:
<223> OTHER INFORMATION: Synthetically generated oligonucleotide

<400> SEQUENCE: 33
gtcgcaaacg ctccttttt ac                                               22

<210> SEQ ID NO 34
<211> LENGTH: 20
<212> TYPE: DNA
<213> ORGANISM: Artificial Sequence
<220> FEATURE:
<223> OTHER INFORMATION: Synthetically generated oligonucleotide

<400> SEQUENCE: 34
gaaaagaaac acatattgat                                                 20

<210> SEQ ID NO 35
<211> LENGTH: 20
<212> TYPE: DNA
<213> ORGANISM: Artificial Sequence
<220> FEATURE:
<223> OTHER INFORMATION: Synthetically generated oligonucleotide

<400> SEQUENCE: 35
gcgggtcttt acgcatatta                                                 20
```

```
<210> SEQ ID NO 36
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 36
ggctgttaaa tgctttggtc g                                           21

<210> SEQ ID NO 37
<211> LENGTH: 20
<212> TYPE: DNA
<213> ORGANISM: Artificial Sequence
<220> FEATURE:
<223> OTHER INFORMATION: Synthetically generated oligonucleotide

<400> SEQUENCE: 37
ttactccata aacatcatcc                                             20

<210> SEQ ID NO 38
<211> LENGTH: 19
<212> TYPE: DNA
<213> ORGANISM: Artificial Sequence
<220> FEATURE:
<223> OTHER INFORMATION: Synthetically generated oligonucleotide

<400> SEQUENCE: 38
gttgaaaatc aagcattgt                                              19

<210> SEQ ID NO 39
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 39
catagctaga aacaacctgt c                                           21

<210> SEQ ID NO 40
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 40
caatttgtta ttgcgctatt c                                           21

<210> SEQ ID NO 41
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 41
tacctttgac gttgagcg                                               18

<210> SEQ ID NO 42
<211> LENGTH: 19
<212> TYPE: DNA
<213> ORGANISM: Artificial Sequence
<220> FEATURE:
<223> OTHER INFORMATION: Synthetically generated oligonucleotide

<400> SEQUENCE: 42
```
cacataccat ttctagtgc				19

<210> SEQ ID NO 43
<211> LENGTH: 20
<212> TYPE: DNA
<213> ORGANISM: Artificial Sequence
<220> FEATURE:
<223> OTHER INFORMATION: Synthetically generated oligonucleotide

<400> SEQUENCE: 43
tgccgtttgt cttgtacttc				20

<210> SEQ ID NO 44
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 44
attgattaac tgacgagata c				21

<210> SEQ ID NO 45
<211> LENGTH: 20
<212> TYPE: DNA
<213> ORGANISM: Artificial Sequence
<220> FEATURE:
<223> OTHER INFORMATION: Synthetically generated oligonucleotide

<400> SEQUENCE: 45
attttccatc tatatctcac				20

<210> SEQ ID NO 46
<211> LENGTH: 22
<212> TYPE: DNA
<213> ORGANISM: Artificial Sequence
<220> FEATURE:
<223> OTHER INFORMATION: Synthetically generated oligonucleotide

<400> SEQUENCE: 46
gtttacattt ttcaatatat ag				22

<210> SEQ ID NO 47
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 47 tccttttct gttaaaaaat g				21

<210> SEQ ID NO 48
<211> LENGTH: 22
<212> TYPE: DNA
<213> ORGANISM: Artificial Sequence
<220> FEATURE:
<223> OTHER INFORMATION: Synthetically generated oligonucleotide

<400> SEQUENCE: 48
ggtattaatc atggcaaagt tt				22

<210> SEQ ID NO 49
<211> LENGTH: 21
<212> TYPE: DNA
<213> ORGANISM: Artificial Sequence

```
<220> FEATURE:
<223> OTHER INFORMATION: Synthetically generated oligonucleotide

<400> SEQUENCE: 49
tatcaatagt tgaatcgtat a                                              21

<210> SEQ ID NO 50
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 50
aatggcttaa agcacatggg g                                              21

<210> SEQ ID NO 51
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 51
gtaaagaagc gtttgaggct g                                              21

<210> SEQ ID NO 52
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 52
gtacttttat attttgattg c                                              21

<210> SEQ ID NO 53
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 53
gaagggattc gctatggc                                                  18

<210> SEQ ID NO 54
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 54
aatatagcac aataagga                                                  18

<210> SEQ ID NO 55
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 55
tgtcatgctg tgtgttatta t                                              21
```

```
<210> SEQ ID NO 56
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 56
caagcacatc attgtattcc g                                             21

<210> SEQ ID NO 57
<211> LENGTH: 22
<212> TYPE: DNA
<213> ORGANISM: Artificial Sequence
<220> FEATURE:
<223> OTHER INFORMATION: Synthetically generated oligonucleotide

<400> SEQUENCE: 57
acctaattta cgcgattcac tg                                            22

<210> SEQ ID NO 58
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 58
cgttttaaat acattatttt g                                             21

<210> SEQ ID NO 59
<211> LENGTH: 22
<212> TYPE: DNA
<213> ORGANISM: Artificial Sequence
<220> FEATURE:
<223> OTHER INFORMATION: Synthetically generated oligonucleotide

<400> SEQUENCE: 59
ttatttatgt gtcggttgtt tc                                            22

<210> SEQ ID NO 60
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 60
ttacatagga ggacctctaa g                                             21

<210> SEQ ID NO 61
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 61
gtgattacat ctgtcattgc g                                             21

<210> SEQ ID NO 62
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 62
```

```
cgcaatgaca gatgtaatca c                                          21

<210> SEQ ID NO 63
<211> LENGTH: 20
<212> TYPE: DNA
<213> ORGANISM: Artificial Sequence
<220> FEATURE:
<223> OTHER INFORMATION: Synthetically generated oligonucleotide

<400> SEQUENCE: 63
tgtgcttgtg atacagcgtg                                            20

<210> SEQ ID NO 64
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 64
tatgcttcat tacgcatcac c                                          21

<210> SEQ ID NO 65
<211> LENGTH: 20
<212> TYPE: DNA
<213> ORGANISM: Artificial Sequence
<220> FEATURE:
<223> OTHER INFORMATION: Synthetically generated oligonucleotide

<400> SEQUENCE: 65
tatttggaaa gcacgattac                                            20

<210> SEQ ID NO 66
<211> LENGTH: 20
<212> TYPE: DNA
<213> ORGANISM: Artificial Sequence
<220> FEATURE:
<223> OTHER INFORMATION: Synthetically generated oligonucleotide

<400> SEQUENCE: 66
gtaatcgtgc tttccaaata                                            20

<210> SEQ ID NO 67
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 67
tgtctaacga agatgcagga c                                          21

<210> SEQ ID NO 68
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 68
ttcatattct gcaatagcct g                                          21

<210> SEQ ID NO 69
<211> LENGTH: 20
<212> TYPE: DNA
<213> ORGANISM: Artificial Sequence
```

```
<220> FEATURE:
<223> OTHER INFORMATION: Synthetically generated oligonucleotide

<400> SEQUENCE: 69
gttgcgcatg tgtcgatatc                                              20

<210> SEQ ID NO 70
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 70
ggtggctata ttggttataa c                                            21

<210> SEQ ID NO 71
<211> LENGTH: 19
<212> TYPE: DNA
<213> ORGANISM: Artificial Sequence
<220> FEATURE:
<223> OTHER INFORMATION: Synthetically generated oligonucleotide

<400> SEQUENCE: 71
atgttccttt aaaatcaat                                               19

<210> SEQ ID NO 72
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 72
ttggcattgg tattatttta c                                            21

<210> SEQ ID NO 73
<211> LENGTH: 19
<212> TYPE: DNA
<213> ORGANISM: Artificial Sequence
<220> FEATURE:
<223> OTHER INFORMATION: Synthetically generated oligonucleotide

<400> SEQUENCE: 73
gaattctata tttgccgct                                               19

<210> SEQ ID NO 74
<211> LENGTH: 22
<212> TYPE: DNA
<213> ORGANISM: Artificial Sequence
<220> FEATURE:
<223> OTHER INFORMATION: Synthetically generated oligonucleotide

<400> SEQUENCE: 74
caacctgcga tgcgtgttta at                                           22

<210> SEQ ID NO 75
<211> LENGTH: 22
<212> TYPE: DNA
<213> ORGANISM: Artificial Sequence
<220> FEATURE:
<223> OTHER INFORMATION: Synthetically generated oligonucleotide

<400> SEQUENCE: 75
attaaacacg catcgcaggt tg                                           22
```

```
<210> SEQ ID NO 76
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 76
ctgttgttgg aacgctaggt a                                              21

<210> SEQ ID NO 77
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 77
ttaggggaca gcttcaggcc a                                              21

<210> SEQ ID NO 78
<211> LENGTH: 20
<212> TYPE: DNA
<213> ORGANISM: Artificial Sequence
<220> FEATURE:
<223> OTHER INFORMATION: Synthetically generated oligonucleotide

<400> SEQUENCE: 78
ttatttttat gtttgacttt                                                20

<210> SEQ ID NO 79
<211> LENGTH: 20
<212> TYPE: DNA
<213> ORGANISM: Artificial Sequence
<220> FEATURE:
<223> OTHER INFORMATION: Synthetically generated oligonucleotide

<400> SEQUENCE: 79
aaagtcaaac ataaaaataa                                                20

<210> SEQ ID NO 80
<211> LENGTH: 20
<212> TYPE: DNA
<213> ORGANISM: Artificial Sequence
<220> FEATURE:
<223> OTHER INFORMATION: Synthetically generated oligonucleotide

<400> SEQUENCE: 80
gttattgatg cacgtcttgg                                                20

<210> SEQ ID NO 81
<211> LENGTH: 19
<212> TYPE: DNA
<213> ORGANISM: Artificial Sequence
<220> FEATURE:
<223> OTHER INFORMATION: Synthetically generated oligonucleotide

<400> SEQUENCE: 81
acgaaaataa acagtgtct                                                 19

<210> SEQ ID NO 82
<211> LENGTH: 20
<212> TYPE: DNA
<213> ORGANISM: Artificial Sequence
<220> FEATURE:
<223> OTHER INFORMATION: Synthetically generated oligonucleotide

<400> SEQUENCE: 82
```
aagacactgt ttattttcgt                                              20

<210> SEQ ID NO 83
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 83
tcggaatcat taatttgaga t                                            21

<210> SEQ ID NO 84
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 84
taactttatt aatatagatg a                                            21

<210> SEQ ID NO 85
<211> LENGTH: 17
<212> TYPE: DNA
<213> ORGANISM: Artificial Sequence
<220> FEATURE:
<223> OTHER INFORMATION: Synthetically generated oligonucleotide

<400> SEQUENCE: 85
aggtcaaacg tctaccc                                                 17

<210> SEQ ID NO 86
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 86
aaaagtcagt tggcgatg                                                18

<210> SEQ ID NO 87
<211> LENGTH: 20
<212> TYPE: DNA
<213> ORGANISM: Artificial Sequence
<220> FEATURE:
<223> OTHER INFORMATION: Synthetically generated oligonucleotide

<400> SEQUENCE: 87
aatgatattg aaatacagcg                                              20

<210> SEQ ID NO 88
<211> LENGTH: 20
<212> TYPE: DNA
<213> ORGANISM: Artificial Sequence
<220> FEATURE:
<223> OTHER INFORMATION: Synthetically generated oligonucleotide

<400> SEQUENCE: 88
aggtcgtgta ctgtcagtca                                              20

<210> SEQ ID NO 89
<211> LENGTH: 20
<212> TYPE: DNA
<213> ORGANISM: Artificial Sequence

```
<220> FEATURE:
<223> OTHER INFORMATION: Synthetically generated oligonucleotide

<400> SEQUENCE: 89
acgtggtgaa ctgccagtga                                                    20
```